US010702533B2

(12) United States Patent
Yun et al.

(10) Patent No.: US 10,702,533 B2
(45) Date of Patent: *Jul. 7, 2020

(54) TREATMENT OF CONDITIONS THROUGH PHARMACOLOGICAL MODULATION OF THE AUTONOMIC NERVOUS SYSTEM

(71) Applicant: Palo Alto Investors, Palo Alto, CA (US)

(72) Inventors: Anthony Joonkyoo Yun, Menlo Park, CA (US); Patrick Yuarn-Bor Lee, Menlo Park, CA (US)

(73) Assignee: Palo Alto Investors, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/414,509

(22) Filed: Jan. 24, 2017

(65) Prior Publication Data

US 2017/0128457 A1 May 11, 2017

Related U.S. Application Data

(63) Continuation of application No. 13/454,902, filed on Apr. 24, 2012, now Pat. No. 9,585,851, which is a continuation of application No. 10/748,897, filed on Dec. 29, 2003, now abandoned.

(60) Provisional application No. 60/510,008, filed on Oct. 8, 2003.

(51) Int. Cl.

| *A61K 31/5377* | (2006.01) |
| *A61K 31/403*  | (2006.01) |
| *A61K 31/138*  | (2006.01) |
| *A61K 9/00*    | (2006.01) |
| *A61K 31/165*  | (2006.01) |
| *A61K 31/166*  | (2006.01) |
| *A61K 31/167*  | (2006.01) |
| *A61K 31/216*  | (2006.01) |
| *A61K 31/255*  | (2006.01) |
| *A61K 31/404*  | (2006.01) |
| *A61K 45/06*   | (2006.01) |
| *A61N 1/36*    | (2006.01) |
| *G06F 19/00*   | (2018.01) |

(52) U.S. Cl.
CPC ........ *A61K 31/5377* (2013.01); *A61K 9/0053* (2013.01); *A61K 31/138* (2013.01); *A61K 31/165* (2013.01); *A61K 31/166* (2013.01); *A61K 31/167* (2013.01); *A61K 31/216* (2013.01); *A61K 31/255* (2013.01); *A61K 31/403* (2013.01); *A61K 31/404* (2013.01); *A61K 45/06* (2013.01); *A61N 1/3606* (2013.01); *A61N 1/36007* (2013.01); *A61N 1/36071* (2013.01); *G06F 19/3456* (2013.01)

(58) Field of Classification Search
CPC .. A61K 31/138; A61K 31/165; A61K 31/166; A61K 31/167; A61K 31/216; A61K 31/255; A61K 31/403; A61K 31/404; A61K 31/5377; A61K 45/06; A61N 1/36007; A61N 1/3606; A61N 1/36071; G06F 19/3456

See application file for complete search history.

(56) References Cited

U.S. PATENT DOCUMENTS

| 4,011,316 A | 3/1977 | Barton |
| 5,015,641 A | 5/1991 | Andrews et al. |
| 5,188,104 A | 2/1993 | Wernicke et al. |
| 5,215,086 A | 6/1993 | Terry, Jr. et al. |
| 5,231,988 A | 8/1993 | Wernicke et al. |
| 5,263,480 A | 11/1993 | Wernicke et al. |
| 5,269,303 A | 12/1993 | Wernicke et al. |
| 5,330,515 A | 7/1994 | Rutecki et al. |
| 5,335,657 A | 8/1994 | Terry, Jr. et al. |
| 5,419,338 A | 5/1995 | Sarma et al. |
| 5,540,730 A | 7/1996 | Terry, Jr. et al. |
| 5,571,150 A | 11/1996 | Wernicke et al. |
| 5,707,400 A | 1/1998 | Terry, Jr. et al. |
| 5,978,702 A | 11/1999 | Ward et al. |
| 6,253,109 B1 | 6/2001 | Gielen |
| 6,284,800 B1 | 9/2001 | Broder et al. |
| 6,329,241 B1 | 12/2001 | Lin |
| 6,337,997 B1 | 1/2002 | Rise |
| 6,356,784 B1 | 3/2002 | Lozano et al. |
| 6,366,813 B1 | 4/2002 | DiLorenzo |
| 6,429,217 B1 | 8/2002 | Puskas |
| 6,449,507 B1 | 9/2002 | Hill et al. |
| 6,459,936 B2 | 10/2002 | Fischell et al. |
| 6,480,743 B1 | 11/2002 | Kirkpatrick et al. |

(Continued)

OTHER PUBLICATIONS

Udobi et al. American Family Physician, Jan. 15, 2003, 67, 2, p. 315-322.*
Stanford Children's Health, 2019 (Year: 2019).*
Corgard, Squibb, 1980, p. 64 (Year: 1980).*
FDA, 1995 (Year: 1995).*
Buchhorn, J of Food, Nutrition and Population Health, 2017 (Year: 2017).*
Frobel et al, Cochrane database of systematic reviews, 2009 (Year: 2009).*
Harvard Health Letter, 2011 (Year: 2011).*
Cecil Textbook of Medicine, 2000 (Year: 2000).*
Johnson et al., (British J. of Cancer 2001, p. 1424-1431) (Year: 2001).*

(Continued)

*Primary Examiner* — Umamaheswari Ramachandran
(74) *Attorney, Agent, or Firm* — Peter W. Schroen; Bret E. Field; Bozicevic, Field & Francis LLP

(57) ABSTRACT

Methods are provided for treating a subject for a condition caused by an abnormality in the subject's autonomic nervous system. In accordance with the subject methods, at least a portion of a subject's autonomic nervous system is pharmacologically modulated with at least one beta-blocker in a manner that is effective to treat the subject for the condition. The subject methods find use in the treatment of a variety of different conditions, where such conditions include various disease conditions. Also provided are systems and kits for use in practicing the subject methods.

12 Claims, No Drawings

(56) References Cited

U.S. PATENT DOCUMENTS

| | | |
|---|---|---|
| 6,484,059 B2 | 11/2002 | Gielen |
| 6,526,318 B1 | 2/2003 | Ansarinia |
| 6,609,025 B2 | 8/2003 | Barrett et al. |
| 6,885,888 B2 | 4/2005 | Rezai |
| 7,363,076 B2 | 4/2008 | Yun et al. |
| 2002/0107553 A1 | 8/2002 | Hill et al. |
| 2002/0177882 A1 | 11/2002 | DiLorenzo |
| 2003/0018367 A1 | 1/2003 | DiLorenzo |
| 2003/0144709 A1 | 7/2003 | Zabara et al. |
| 2003/0171391 A1 | 9/2003 | Gaida et al. |
| 2004/0111033 A1 | 6/2004 | Oung et al. |
| 2004/0147969 A1 | 7/2004 | Mann et al. |
| 2005/0215533 A1 | 9/2005 | Gottlieb et al. |

OTHER PUBLICATIONS

Gura et al. (Science 1997, Nov. 7, 278) (Year: 1997).*
Allen Am J of Medicine, 1975, p. 199-208 (Year: 1975).*
Abraham, Congestive Heart Failure, 2003 (Year: 2003).*
Crosby, Cochrane Library, 2003 (Year: 2003).*
DiNicolantonio et al. (OpenHeart, 2015) (Year: 2015).*
Akbar, Asian Pacific J of Cancer Prevention, 15, 2014 (Year: 2014).*
Drug Class Review, 2009 (Year: 2009).*
"What are an Agonist and Antagonist?", http://www.gallusdetox.com/suboxone-detox-resources/513-what-are-an-agonist-and-antagonist, accessed on May 29, 2015, 2 pages.
Abraham, Switching between beta blockers in heart failure patients: rationale and practical considerations, Congest Heart Fail. Sep.-Oct. 2003;9(5):271-8.
Akbar et al., Are Beta Blockers New Potential Anticancer Agents?, Asian Pac J Cancer Prev 15 (22), 9567-9574.
Antagonist, http://www.oxforddictionaries.com/us/definition/american_english/antagonist, Jun. 2014, 2 pages.
Aronson et al., Effect of beta-blockade on heart rate variability in decompensated heart failure, Int J Cardiol. Jun. 2001;79(1):31-9.
Barendregt et al., Parasympathetic dysfunction in rheumatoid arthritis patients with ocular dryness, Ann Rheum Dis. Sep. 1996;55(9):612-5.
Brevetti et al., Effective treatment of orthostatic hypotension by propranolol in the Shy-Drager syndrome, American Heart Journal vol. 102, Issue 5, Nov. 1981, pp. 938-941.
Bugiardini et al., Comparison of verapamil versus propranolol therapy in syndrome X, Am J Cardiol. Feb. 1, 1989;63(5):286-90.
Burger et al., Effect of beta adrenergic receptor blockade on cardiac autonomic tone in patients with chronic stable angina, Pacing Clin Electrophysiol. Apr. 1996;19(4 Pt 1):411-7.
Chester et al., Adverse effect of propranolol on airway function in nonasthmatic chronic obstructive lung disease, Chest. May 1981;79(5):540-4.
Crosby et al., Beta-blocker therapy for tremor in Parkinson's disease, Cochrane Database Syst Rev. 2003;(1):CD003361.
Davies et al., Effect of ibuprofen on blood pressure control by propranolol and bendrofluazide, J Int Med Res. May-Jun. 1988;16(3):173-81.
Dinicolantonio et al., β-Blockers in hypertension, diabetes, heart failure and acute myocardial infarction: a review of the literature, Open Heart (2015), 2:e000230, p. 1-12.
Gambardella et al., Intralipid infusion combined with propranolol administration has favorable metabolic effects in elderiy malnourished cancer patients, Metabolism. Mar. 1999:48(3):291-7.
Garrett et al., Factors affecting the secretion of submandibular salivary kallikrein in cats, Q J Exp Physiol. Jul. 1987;72(3):357-68.
Gulli et al., Evidence of parasympathetic impairment in some patients with cardiac syndrome X, Cardiovasc Res. Nov. 2001;52(2):208-16.
Houston, Adverse effects of antihypertensive drug therapy on glucose intolerance, Cardiol Clin. Feb. 1986;4(1):117-35.
http://en.wikipedia.org/wiki/Propranolol.

Jatoi et al., Current management of cancer-associated anorexia and weight loss, Oncology (Williston Park). Apr. 2001:15(4):497-502.
Kallio, Cardiovascular Autonomic Dysfunction in Parkinsonian Syndromes, Chapter 2. Review of the literature, 2.4. Methods for assessing autnomic functions, Review, Duke Univ. 2000.
Kau et al., Acute effects of digoxin on plasma aldosterone and cortisol in monkeys, Metabolism. Jan. 2009;58(1):55-61.
Kau et al., Inhibitory effects of digoxin and ouabain on aldosterone synthesis in human adrenocortical NCI-H295 cells, J Cell Physiol. Dec. 2005;205(3):393-401.
Lampert et al., Effects of propranolol on recovery of heart rate variability following acute myocardial infarction and relation to outcome in the Beta-Blocker Heart Attack Trial, Am J Cardiol. Jan. 15, 2003;91(2):137-42.
Lauer, Autonomic function and prognosis, Cleve Clin J Med Apr. 2009;76 Suppl 2:S18-22.
Levine et al., Beta 2-adrenergic mechanisms in experimental arthritis, Proc Natl Acad Sci U S A. Jun. 1988; 85(12): 4553-4556.
Lieberman et al., The possible adverse effect of propranolol on the fetus in pregnancies complicated by severe hypertension, Br J Obstet Gynaecol. Sep. 1978;85(9):678-83.
Majcherczyk et al., Increase of renal sympathetic nerve activity by metoprolol or propranolol in conscious spontaneously hypertensive rats, Br J Pharmacol. Aug. 1987; 91(4): 711-714.
McBride et al., Supraventricular tachycardia treated with continuous infusions of propranolol, Clin Pharmacol Ther. Jul. 1988;44(1):93-9.
McDowell et al., Anthropometric Reference Data for Children and Adults: United States, 2003-2006, Natl Health Stat Report Oct. 22, 2008;(10):1-48.
McQueen et al., Effects of paracetamol and aspirin on neural activity of joint mechanonociceptors in adjuvant arthritis, Br. J. Pharmacol. vol. 104, Issue 1, Sep. 1991, pp. 178-182.
Mehmanesh et al., Temporary atrial electrode for the treatment of supraventricular tachycardia after cardiac operations, Ann Thorac Surg. Mar. 1998;65(3):632-6.
Morita et al., Evaluation of autonomic nervous activity in patients with congenital long QT syndrome by an analysis of RR variability, Jpn Circ J. Oct. 1996;60(10):742-8.
Mueller et al., Propranolol during the evolution and subsequent ten days of myocardial infarction in man: hemodynamic, initial cardiac energetic, and neurohumoral responses, Clin Cardiol. Dec. 1979;2(6):393-403.
Non-steroidal anti-inflamatroy, Wikipedia, http://en.wikipedia.org/wiki/Non-steroidal)anti-inflammatory_drug), p. 1-9.
Nordling et al., Role of the autonomic nervous system in catheter-induced urethral inflammation, European Urology 21(4):328-31—Feb. 1992.
Okopski, Recent advances in pharmaceutical chemistry—review. III. A new wave of beta-blockers, J Clin Pharm Ther. Dec. 1987;12(6):369-88.
Perry et al., Altered autonomic function in patients with arthritis or with chronic myofascial pain, Pain, vol. 39, Issue 1, Oct. 1989, pp. 77-84.
Rang et al., Non-invasive assessment of autonomic cardiovascular control in normal human pregnancy and pregnancy-associated hypertensive disorders: a review, J Hypertens. Nov. 2002;20(11):2111-9.
Salpeter et al., Cardioselective beta-blockers for reversible airway disease, Cochrane Database Syst Rev. 2002;(4):CD0002992.
Savola, Arthropathy induced by beta blockade, Br Med J (Clin Res Ed). Oct. 29, 1983; 287(6401): 1256-1257.
Schneider et al., Plasma propranolol concentrations and the erythrocyte sedimentation rate, Br J Clin Pharmacol. Jul. 1979;8(1):43-7.
Self et al., Noncardioselective Beta-Blocker Use in Patients With Asthma: Are We Vigilant?, Consultant: vol. 52—Issue 9—Sep. 2012.
Shimizu et al., Differential effects of beta-blockade on dispersion of repolarization in the absence and presence of sympathetic stimulation between the LQT1 and LQT2 forms of congenital long QT syndrome, J Am Coll Cardiol. Jun. 19, 2002;39(12):1984-91.
Stockley, Are beta blockers and nifedipine safe?, BMJ 1989;298:1584.
Waller et al., Intravenous propranolol in patients with inflammation, Br J Clin Pharmacol. Apr. 1982; 13(4): 577-578.

(56) References Cited

OTHER PUBLICATIONS

Walpole et al., The weight of nations: an estimation of adult human biomass, BMC Public Health. Jun. 18, 2012;12:439.
Walsh et al., Autonomic nervous system dysfunction in advanced cancer, Support Care Cancer. Oct. 2002;10 (7):523-8.
Winchell et al., Spectral analysis of heart rate variability in the ICU: a measure of autonomic function, J Surg Res. Jun. 1996;63(1):11-6.
Frishman et al., Current cardiovascular drugs, 7 Beta-Adrenergic Blockers, Philadelphia, Pa: Current Medicine, 2000, p. 152.
Van Der Jagt et al., Beta-blockers in Intensive Care Medicine: Potential Benefit in Acute Brain Injury and Acute Respiratory Distress Syndrome, Recent Patents on Cardiovascular Drug Discovery, 2012, 7, 141-151.
Vaillancourt et al., Autonomic nervous system involvement in pulmonary arterial hypertension, Respiratory Research (2017) 18:201.

\* cited by examiner

TREATMENT OF CONDITIONS THROUGH PHARMACOLOGICAL MODULATION OF THE AUTONOMIC NERVOUS SYSTEM

CROSS REFERENCE TO RELATED APPLICATIONS

The present application claims priority under 35 U.S.C. § 119(e) to U.S. provisional application No. 60/510,008, entitled "Treatment of Conditions Through Electrical or Pharmacologic Modulation of the Autonomic Nervous System" to Yun et al., filed Oct. 8, 2003, the disclosure of which is incorporated herein by reference in its entirety.

FIELD OF THE INVENTION

The field of this invention is the treatment of conditions associated with the autonomic nervous system and more specifically the treatment of conditions through pharmacological modulation of the autonomic nervous system.

BACKGROUND OF THE INVENTION

There are a variety of conditions that can affect an individual's health and well-being. The treatment of various conditions that affect the health and well-being of an individual has been around for centuries. In general, the armament of treatment options available to a physician to treat such conditions has increased tremendously, especially in the last century.

However, while the number of treatment options has increased, typically such options are merely palliative, i.e., are designed for the relief of symptoms of a condition rather than actually being curative of the disorder itself. In fact, treatment protocols effectively directed at the underlying cause of a condition are quite rare.

As such, there continues to be an interest in the development of new protocol options for treating conditions.

SUMMARY OF THE INVENTION

Methods are provided for treating a subject for a condition caused by an abnormality in the subject's autonomic nervous system. In accordance with the subject methods, at least a portion of a subject's autonomic nervous system is pharmacologically modulated with at least one beta-blocker in a manner that is effective to treat the subject for the condition. The subject methods find use in the treatment of a variety of different conditions, where such conditions include various disease conditions. Also provided are systems and kits for use in practicing the subject methods.

DETAILED DESCRIPTION OF THE INVENTION

Methods are provided for treating a subject for a condition caused by an abnormality in the subject's autonomic nervous system. In accordance with the subject methods, at least a portion of a subject's autonomic nervous system is pharmacologically modulated with at least one beta-blocker in a manner that is effective to treat the subject for the condition. The subject methods find use in the treatment of a variety of different conditions, where such conditions include various disease conditions. Also provided are systems and kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

As summarized above, the subject invention provides methods for treating a subject for a condition caused by an abnormality in the subject's autonomic nervous system by pharmacologically modulating at least a portion of the subject's autonomic nervous system. In further describing the subject invention, representative embodiments of the subject methods are described first in greater detail, followed by a review of various representative applications in which the subject methods may find use. Next, a review of systems and kits for use in the subject methods is provided.

Methods

As noted above, the subject methods are methods for treating a subject for a condition caused by an autonomic nervous system abnormality. More specifically, the subject methods are methods for treating a subject for a condition caused by an abnormality in a subject's autonomic nervous system by pharmacologically modulating at least a portion of the subject's autonomic nervous system. Embodiments include pharmacologically modulating at least a portion of the autonomic nervous system to inhibit activity in at least a portion of the autonomic nervous system, e.g., inhibit activity in at least a portion of the sympathetic nervous system, by administering an effective amount of at least one beta-blocker in a manner effective to treat the subject for the condition.

Up until now, scientists have viewed biology as a complex system of daunting degree. Seemingly endless new relationships between various pathways are constantly emerging during research and seem to variously confirm and refute previous assumptions. This type of bottoms-up approach to biology has led to a perception that human biology and human diseases are perhaps too complex to successfully comprehend with current scientific knowledge. New data is often thought to add degrees of complexity to the understanding of biology and disease. More and more focus of modern biology is on diversity and variance of normal and abnormal biology.

The inventors of the subject invention have discovered that, in fact, many, if not all, human medical conditions, including diseases, are actually governed by a coherent set of simple rules. In other disciplines, it has been mathematically shown that seemingly complex patterns can emerge from simple rules. The inventors of the subject invention have realized that the complex myriad of seemingly unrelated human diseases are actually governed by simple unifying concepts. The inventors of the subject invention have thus approached biology, not as bottoms up exercise of collecting and analyzing complex data sets, but rather, as a top down process of identifying simple unifying principles that manifest in complex downstream biology. Such upstream analysis has enabled the inventors of the subject invention to look at science at the meta-level, and the study of science at this higher stratum has yielded surprising answers to the nature of human biology and disease, and thus to novel treatment options for various human conditions, including diseases. The inventors of the subject invention have discovered that autonomic nervous system disturbance, or abnormalities of the autonomic nervous system, is the simple rule that governs a wide range of conditions (including diseases) that, when viewed from a clinical standpoint, appear to be a complex, heterogeneous, unrelated group. The inventors of the subject invention have discovered otherwise and have formulated novel pharmacologic strategies to treat conditions including disease conditions by modulating autonomic function as the basis of therapy.

Accordingly, embodiments of the subject invention include pharmacologically modulating at least a portion of a subject's autonomic nervous system to at least inhibit activity in a portion of the autonomic nervous system, e.g., in at least a portion of the sympathetic nervous system. In accordance with the subject invention, modulating at least a portion of autonomic nervous system may be achieved by administering an effective amount of at least one beta-blocker. Accordingly, the subject methods include administering an effective amount of at least one beta-blocker to a subject to inhibit activity in at least a portion of a subject's sympathetic nervous system to effectively treat the subject for a condition.

Specifically, the subject invention includes pharmacologically modulating at least a portion of a subject's autonomic nervous system by administering an effective amount of at least one beta-blocker to achieve a desired parasympathetic activity/sympathetic activity ratio, i.e., a desired balance between parasympathetic activity and sympathetic activity, e.g., a balance analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided or desired by the subject invention may be analogous to the parasympathetic activity/sympathetic activity ratio observed in a healthy human ranging in age from about 20 years old to about 25 years old.

Before further describing the subject methods, the autonomic nervous system is reviewed to provide a proper foundation for the subject invention.

Review of the Autonomic Nervous System

The nervous system is divided into the somatic nervous system and the autonomic nervous system ("ANS"). In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organisms' internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs; lungs; stomach; colon; bladder; visual accommodation, secretions from exocrine and endocrine glands, etc. The ANS does this through a series of nerve fibers and more specifically through efferent and afferent nerves. The ANS acts through a balance of its two components: the sympathetic nervous system and parasympathetic nervous system, which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The Parasympathetic System

The parasympathetic nervous system is the part of the autonomic nervous system controlling a variety of autonomic functions including, but not limited to, involuntary muscular movement of blood vessels and gut and glandular secretions from eye, salivary glands, bladder, rectum and genital organs. The vagus nerve is part of the parasympathetic system. Parasympathetic nerve fibers are contained within the last five cranial nerves and the last three spinal nerves and terminate at parasympathetic ganglia near or in the organ they supply. The actions of the parasympathetic system are broadly antagonistic to those of the sympathetic system, lowering blood pressure, slowing heartbeat, stimulating the process of digestion etc. The chief neurotransmitter in the parasympathetic system is acetylcholine.

More specifically, neurons of the parasympathetic nervous system emerge from the brainstem as part of the Cranial nerves III, VII, IX and X (vagus nerve) and also from the sacral region of the spinal cord via Sacral nerves 2, 3 and 4. Because of these origins the parasympathetic nervous system is often referred to as the 'craniosacral outflow'.

In the parasympathetic nervous system both pre- and postganglionic neurons are cholinergic (i.e., they utilize the neurotransmitter acetylcholine) Unlike adrenaline and noradrenaline, which the body takes around 90 minutes to metabolize, acetylcholine is rapidly broken down after release by the enzyme cholinesterase. As a result the effects are relatively brief in comparison to the sympathetic nervous system.

Each preganglionic parasympathetic neuron synapses with just a few postganglionic neurons, which are located near—or in—the effector organ, a muscle or gland. As noted above, the primary neurotransmitter in the parasympathetic system is acetylcholine ("Ach") such that ACh is the neurotransmitter at all the pre- and many of the postganglionic neurons of the parasympathetic system. However, some of the postganglionic neurons release nitric oxide as their neurotransmitter.

The Sympathetic System

The sympathetic nervous system is the part of the autonomic nervous system comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The sympathetic nervous system controls a variety of autonomic functions including, but not limited to, control of movement and secretions from viscera and monitoring their physiological state, stimulation of the sympathetic system inducing e.g. the contraction of gut sphincters, heart muscle and the muscle of artery walls, and the relaxation of gut smooth muscle and the circular muscles of the iris. The chief neurotransmitter in the sympathetic system is adrenaline which is liberated in the heart, visceral muscle, glands and internal vessels, with acetylcholine acting as a neurotransmitter at ganglionic synapses and at sympathetic terminals in skin and skeletal muscle blood vessels. The actions of the sympathetic system tend to be antagonistic to those of the parasympathetic system.

More specifically, the preganglionic motor neurons of the sympathetic system arise in the spinal cord. They pass into sympathetic ganglia which are organized into two chains that run parallel to and on either side of the spinal cord. The neurotransmitter of the preganglionic sympathetic neurons is acetylcholine ("Ach") which stimulates action potentials in the postganglionic neurons.

The neurotransmitter released by the postganglionic neurons is nonadrenaline (also called norepinephrine). The action of noradrenaline on a particular structure such as a gland or muscle is excitatory is some cases, inhibitory in others. At excitatory terminals, ATP may be released along with noradrenaline.

Activation of the sympathetic system may be characterized as general because a single preganglionic neuron usually synapses with many postganglionic neurons and the release of adrenaline from the adrenal medulla into the blood ensures that all the cells of the body will be exposed to sympathetic stimulation even if no postganglionic neurons reach them directly.

Methods of Treating a Subject for a Condition

As indicated above, the subject invention provides methods of treating a subject for a condition associated with the autonomic nervous system and more specifically the treatment of a condition through pharmacological modulation of the autonomic nervous system that includes administration of at least one beta-blocker. Embodiments include treating a subject for a condition caused by an abnormality in the subject's autonomic nervous system by pharmacologically modulating at least a portion of the subject's autonomic nervous system to at least decrease or inhibit sympathetic activity, i.e., to increase the parasympathetic activity/sympathetic activity ratio or increase parasympathetic activity relative to sympathetic activity in at least a portion of the autonomic nervous system. By "pharmacologically modulating at least a portion of a subject's autonomic nervous system" is meant altering or changing at least a portion of an autonomic nervous system by pharmacological means to provide a change, alteration or shift in at least one component or aspect of the autonomic nervous system, as will be described in greater detail below. The pharmacological modulation of the autonomic nervous system may affect central motor output and/or nerve conduction and/or transmitter release and/or synaptic transmission and/or receptor activation, but in any event is a change that provides an increase in the parasympathetic activity/sympathetic activity ratio (as used herein, "activity" and "function" are used interchangeably), at least by inhibiting or decreasing sympathetic activity.

For example, embodiments include pharmacologically modulating at least a portion of a subject's autonomic nervous system to alter, shift or change parasympathetic activity and/or sympathetic activity from a first state to a second state, where the second state is characterized at least by a decrease or inhibition of at least a portion of the sympathetic nervous system relative to the first state, e.g., an increase in the parasympathetic activity/sympathetic activity ratio relative to the first state. Embodiments include pharmacological methods of decreasing activity in at least one sympathetic nerve fiber to achieve a decrease in at least a portion of the sympathetic system, e.g., to increase the parasympathetic activity/sympathetic activity ratio. Accordingly, embodiments include pharmacologically inhibiting activity in at least one sympathetic nerve fiber to achieve an increased parasympathetic activity relative to sympathetic activity. Embodiments of the subject invention include administering an effective amount of one or more pharmacological agents (at least one of which is a beta-blocker) to both increase activity in at least a portion of the parasympathetic system, e.g., increase activity in at least one parasympathetic nerve fiber, and inhibit activity in at least a portion of the sympathetic nervous system, e.g., in at least one sympathetic nerve fiber, to treat a condition caused at least in part by an abnormality in the subject's autonomic nervous system.

Accordingly, a feature of embodiments of the subject methods is that the ratio of parasympathetic activity to sympathetic activity is increased by at least decreasing or inhibiting activity or function in at least a portion of the sympathetic nervous system by administration of at least one beta-blocker. By "increased ratio of parasympathetic activity to sympathetic activity" is meant that this ratio (characterized by parasympathetic activity/sympathetic activity) is increased in at least a portion of the autonomic nervous system, where the increase is at least great enough to provide the desired results, e.g., great enough to treat a given condition. For example, in certain embodiments a subject may have an abnormal ratio of parasympathetic/sympathetic activity and the subject invention may be employed to adjust this ratio.

While the ratio of parasympathetic function/sympathetic function may be increased according to embodiments of the subject invention, the net result may be a parasympathetic bias (i.e., parasympathetic dominance), sympathetic bias (i.e., sympathetic dominance) or the activities of the parasympathetic system and sympathetic system may be substantially equal (i.e., neither is dominant). By "bias" is meant that the particular "biased" component of the autonomic nervous system has a higher activity level than the other component. For example, a sympathetic bias refers to a higher level of sympathetic activity than parasympathetic activity at least in a portion of the autonomic nervous system, and vice versa, where such bias may be systemic or localized. Accordingly, the net result of treating a condition by modulating at least a portion of a subject's autonomic nervous system to increase the parasympathetic activity/sympathetic activity ratio by administering an effective amount of at least one beta-blocker may be higher or greater sympathetic activity relative to parasympathetic activity in at least the area of the autonomic system targeted or rather in need of modulation, higher or greater parasympathetic activity relative to sympathetic activity in at least the area of the autonomic system targeted or rather in need of modulation, or substantially equal activity levels of sympathetic activity and parasympathetic activity.

Accordingly, in practicing the subject methods, at least a portion of a subject's autonomic nervous system is pharmacologically modulated with an effective amount of at least one beta-blocker to increase parasympathetic activity relative to sympathetic activity (i.e., increase the parasympathetic activity/sympathetic activity ratio). As noted above, the pharmacological modulation at least provides a decrease in function or dampening of a portion of the autonomic system, e.g., may inhibit activity in at least one sympathetic nerve fiber or inhibit nerve pulse transmission. As the subject methods include pharmacologically modulating at least a portion of a subject's autonomic nervous system, the pharmacological modulation may be systemic or regional (i.e., local). In other words, the entire autonomic nervous system may be modulated (e.g., the entire sympathetic nervous system may be modulated) or only a portion may be modulated (e.g., only a portion of the sympathetic system may be modulated). For example, at least one sympathetic nerve fiber may be modulated by the administration of at least one beta-blocker.

Accordingly, in the practice if the subject invention activity in at least a portion of the sympathetic system may be inhibited to modulate at least a portion of the autonomic nervous system. For example, activity in any portion (or all) of the sympathetic nervous system may be inhibited to increase parasympathetic activity relative to sympathetic activity to provide the desired ratio of parasympathetic/sympathetic activity, e.g., activity in one or more sympathetic nerve fibers may be inhibited. By "inhibited" is meant to include, but is not limited to, disruption, down-regulating, dampening and partial and complete blockage of function or nerve impulses in a particular area of the sympathetic system.

Inhibiting or "down-regulating" activity in at least a part of the sympathetic system may be desired in a variety of instances, where such instances include, but are not limited, abnormal activity in at least a portion of the parasympathetic system and/or the sympathetic system. The subject methods may be employed, for example, in instances where parasympathetic function is normal or abnormally low or high and/or sympathetic function is normal or abnormally low or high. The subject methods may be employed, for example, in instances where parasympathetic function is normal or abnormally high and/or sympathetic function is normal or abnormally low or abnormally high. By "normal" is meant the typical autonomic nervous system functions for a healthy subject, e.g., a healthy human subject ranging in age from about 20 years old to about 25 years old. Such embodiments may be employed to alter the dominance and/or may be employed to modulate the differential between the two systems.

For example, prior to modulating the autonomic system according to the subject invention, the activity in the sympathetic system may be higher than activity in the parasympathetic system and the subject methods may be employed to increase the parasympathetic activity to a level that is greater than the sympathetic activity and/or may be employed to alter the differential or difference in activity levels of the two systems such as decreasing the difference in activity levels or increasing the difference in activity levels which may or may not result in sympathetic activity that is lower than parasympathetic activity. In other embodiments, prior to modulating the autonomic system according to the subject invention, the activity in the parasympathetic system may be higher than activity in the sympathetic system and the subject methods may be employed to alter the differential or difference in activity levels of the two systems such as increasing the difference in activity levels which may or may not result in sympathetic activity that remains lower than parasympathetic activity.

Accordingly, the subject methods may be employed in instances where, prior to the inhibition of activity in, e.g., at least one sympathetic nerve fiber, the sympathetic activity is higher than desired, which may or may not be a normal state. For example, sympathetic activity may be higher than the parasympathetic activity (i.e., there exists a sympathetic bias) or sympathetic activity may be less than or approximately equal to, including equal, to parasympathetic activity, but it is desired to decrease the sympathetic activity even more and the subject methods may be employed to modulate the differential between the parasympathetic-sympathetic systems such that the result of decreasing sympathetic activity may be a sympathetic bias, parasympathetic bias or may be an equalization of the two systems (i.e., the activities of the two systems are approximately equal—including equal), regardless of the state or relative activity levels of the two systems prior to employing the subject methods, but the difference between the parasympathetic-sympathetic systems may be modulated, e.g., increased or reduced in certain embodiments. Accordingly, embodiments of the subject methods may be employed to decrease sympathetic activity below that of parasympathetic activity and/or may be employed to modulate (decrease or increase) the differential between the two systems, but in any event is employed to increase the ratio of parasympathetic activity to sympathetic activity. For example, decreasing activity in at least a portion of the sympathetic system may be employed where there is a normal or an abnormally low parasympathetic function and/or abnormally high sympathetic function. Such may also be desired in instances where, prior to decreasing sympathetic function in, e.g., at least one sympathetic nerve fiber, parasympathetic activity is higher than the sympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present or a relative bias towards parasympathetic function may be present. Other instances include normal or below normal (i.e., abnormally low) parasympathetic activity and/or normal or above normal (i.e., abnormally high) sympathetic activity. The above-described examples of instances where decreasing sympathetic activity may be desired is exemplary only and is in no way intended to limit the scope of the invention and other instances where decreasing sympathetic activity to treat a condition such as a disease are contemplated by the subject invention and will be apparent to those of skill in the art.

As embodiments include pharmacologically modulating a subject's autonomic nervous system to at least inhibit activity in a portion of a subject sympathetic nervous system, it is to be understood that the pharmacological modulation in accordance with the subject invention may be performed prior to and/or at the same time and/or subsequent to any other medical or clinical treatment regime such as, for example, administration of one or more other pharmacological agents (i.e., non beta-blockers), electrical modulation of at least a portion of the subject's autonomic nervous system, e.g., as described in copending U.S. patent application Ser. No. 10/661,368, entitled "Treatment of Conditions Through Electrical Modulation of the Autonomic Nervous System", the disclosure of which is herein incorporated by reference, and the like. In other words, the subject methods may include other concomitant therapies or treatments.

According to embodiments of the subject invention, pharmacological modulation is accomplished by at least administering an effective amount of at least one beta-blocker to a subject to treat the subject for a condition caused, precipitated or otherwise exacerbated, influenced or affected by the amount or magnitude of sympathetic activity in at least a portion of the sympathetic nervous system. In other words, activity in at least a portion of the sympathetic system is at a level that is at least contributing to or otherwise affecting a condition such a disease condition in need of treatment, and as such is in need of reduction or inhibition to treat the condition.

That is, embodiments of the subject methods include administering an effective amount, i.e., a therapeutically effective amount, of one or more beta-blockers to a subject to modulate at least a portion of the subject's autonomic nervous system by at least decreasing activity in at least a portion of the sympathetic nervous system. By "effective amount" is meant a dosage sufficient to modulate at least a portion of a subject's sympathetic nervous system for a given period of time. The effective amount will vary with the age and physical condition of the subject, severity of the condition being treated, the duration of the treatment, the nature of any concurrent treatment, the pharmaceutically acceptable carrier used if any, and analogous factors within the knowledge and expertise of those skilled in the art.

Accordingly, embodiments of the subject invention include administering an effective amount of at least one beta-blocker. In certain embodiments, more than one type of beta-blocker may be administered at the same or different times to treat the same or different condition. The effective amount of a given beta-blocker may vary somewhat from subject to subject, and may depend upon factors such as, but not limited to, the age and condition of the subject, the form of the beta-blocker, the route and method of delivery, etc., as noted above. Such beta-blocker dosages may be determined in accordance with routine pharmacological procedures known to those skilled in the art. For example, beta-blockers and/or adjuvants may be administered to a subject in an amount ranging from about 0.5 milligrams to about 1200 milligrams or more in a single oral dose, one time a day or more for days, weeks, months, years, even as long as a subject's lifetime. For example, embodiment may include administering about 100 milligrams of a given beta-blocker two times a day over a prolonged period of time, e.g., over about 1-3 months, e.g., about 3 months to about 3 years or more, e.g., orally or with a medical infusion pump or similar device designed for delivery of a substance over a prolonged period. The frequency of administration of the one or more beta-blockers may vary depending, e.g., on one or more of the factors described above. For example, the frequency of administration may range from about 1 time per day to multiple times per day, e.g., about 2 times or more per day or as necessary to treat or otherwise control or manage a condition. The duration of therapy depends on the type of condition being treated and may range from as short as about 24 hours to as long as the life of the subject. By "adjuvants" meant a compound that, when used in combination with the one or more beta-blocker compounds and/or compositions, augments or otherwise alters or modifies the resultant pharmacological and/or physiological responses.

Depending on the particular beta-blocker(s) administered to a subject, the beta-blocker(s) may be administered to a subject using any convenient means capable of resulting in the desired modulation of the autonomic nervous system. Thus, the at least one beta-blocker may be incorporated into a variety of formulations for therapeutic administration. More particularly, the beta-blockers may be formulated into pharmaceutical compositions by combination with appropriate, pharmaceutically acceptable carriers. By "pharmaceutically acceptable carrier" is meant a component such as a carrier, diluent, excipient, and the like of a composition that is compatible with the one or more beta-blockers and other optional ingredients of the subject beta-blocker compositions in that a pharmaceutically acceptable carrier may be combined with the beta-blocker(s) without eliminating the biological or therapeutically effective activity of the one or more beta-blockers, and is suitable for use in subjects as provided herein without undue adverse side effects (such as toxicity, irritation, allergic response, and death). Side effects are "undue" when their risk outweighs the benefit provided by the pharmaceutical bet blocker(s). Non-limiting examples of pharmaceutically acceptable components include, but are not limited to, any of the standard pharmaceutical carriers such as phosphate buffered saline solutions, water, emulsions such as oil/water emulsions or water/oil emulsions, microemulsions, and various types of wetting agents. Accordingly, the beta-blockers employed in the subject methods may be formulated into preparations in solid, semi-solid (e.g., gel), liquid or gaseous forms, such as tablets, capsules, powders, granules, ointments, solutions, suppositories, injections, inhalants and aerosols. As such, administration of a beta-blocker may be achieved in various ways, including, but not limited to, oral, buccal (e.g. sublingual), rectal, topical (including both skin and mucosal surfaces, including airway surfaces), parenteral (e.g., subcutaneous, intramuscular, intradermal, intravenous and intrathecal), intraperiactivityal, transdermal, intracheal, intravaginal, endocervical, intrathecal, intranasal, intravesicular, in or on the eye, in the ear canal, etc., administration. In certain embodiments, one or more beta-blockers are administered via a transdermal patch or film system such as or analogous to that described, e.g., in U.S. Pat. Nos. 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; and 4,585,452, the disclosures of which are herein incorporated by reference.

As noted above, embodiments may include pharmaceutical beta-blocker formulations for oral administration that may be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc., suitable for ingestion by the patient. Pharmaceutical preparations for oral use may be obtained through combination of at least one beta-blocker with a solid excipient, optionally grinding a resulting mixture, and processing the mixture of granules, after adding suitable additional compounds, if desired, to obtain tablets or dragee cores. Suitable solid excipients include, but are not limited to, carbohydrate or protein fillers and include, but are not limited to sugars, including lactose, sucrose, mannitol, or sorbitol; starch from corn, wheat, rice, potato, or other plants; cellulose such as methyl cellulose, hydroxypropylmethyl-cellulose or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate; with optional lubricants, such as talc or magnesium stearate; and if desired, with diluents, buffering agents, moistening agents, preservatives and flavoring agents.

Accordingly, beta-blocker formulations suitable for oral administration in accordance with the subject invention may be present in discrete units, such as capsules, cachets, lozenges, tablets, and the like, each containing a predetermined amount of the active beta-blocker; as a powder or granules; as a solution or a suspension in an aqueous or non-aqueous liquid; or as an oil-in-water or water-in-oil emulsion. Such beta-blocker formulations may be prepared by any suitable method of pharmacy which includes, but is not limited to, bringing into association the active beta-blocker and a suitable carrier (which may contain one or more optional ingredients as noted above). For example, beta-blocker formulations for use with the subject invention may be prepared by uniformly and intimately admixing the active beta-blocker(s) with a liquid or finely divided solid carrier, or both, and then, if necessary, shaping the resulting mixture. For example, a tablet may be prepared by compressing or molding a powder or granules containing the active beta-blocker, optionally with one or more accessory ingredients. Compressed tablets may be prepared by compressing, in a suitable machine, the beta-blocker in a free-flowing form, such as a powder or granules optionally mixed with a binder, lubricant, inert diluent, and/or surface active/dispersing agent(s). Molded tablets may be made by molding, in a suitable machine, the powdered beta-blocker moistened with an inert liquid binder.

The beta-blockers of this invention may also be administered in the form of suppositories for rectal administration of the drug. These formulations may be prepared by mixing a beta-blocker with a suitable non-irritating vehicle or excipient which is solid at ordinary temperatures but liquid at the rectal temperatures and will therefore melt in the rectum to release the drug. Such materials include, but are not limited to, cocoa butter, carbowaxes and polyethylene glycols. Embodiments include one or more beta-blocker agent(s) made into suppositories by mixing with a variety of bases such as emulsifying bases or water-soluble bases.

The beta-blockers of this invention may also be administered by in intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

For example, embodiments may also include at least one beta-blocker in an aerosolized, atomized or nebulized vapor form, e.g., administrable via a metered dose device or nebulizer, and the like such that embodiments also include aerosolizing, vaporing or nebulizing one or more beta-blockers for administration to a subject. Accordingly, the one or more beta-blocker agents may be utilized in aerosol formulation or an analogous formulation to be administered via inhalation or analogous means. The one or more beta-blockers employed in the practice of the present invention may be formulated into pressurized acceptable propellants such as dichlorodifluoromethane, propane, nitrogen and the like.

The beta-blockers of the invention may be delivered transdermally, by a topical route, formulated as applicator sticks, solutions, suspensions, emulsions, gels, creams, ointments, pastes, jellies, paints, powders, and aerosols. For example, embodiments may include a beta-blocker formulation in the form of a discrete patch or film or plaster or the like adapted to remain in intimate contact with the epidermis of the recipient for a period of time. For example, such transdermal patches may include a base or matrix layer, e.g., polymeric layer, in which one or more beta-blocker(s) are retained. The base or matrix layer may be operatively associated with a support or backing. Beta-blocker formulations suitable for transdermal administration may also be delivered by iontophoresis and may take the form of an optionally buffered aqueous solution of the beta-blocker compound. Suitable formulations may include citrate or bis/tris buffer (pH 6) or ethanol/water and contain a suitable amount of active ingredient.

The beta-blockers of the invention may also be delivered as microspheres for slow release in the body. For example, microspheres may be administered via intradermal injection of drug-containing microspheres, which slowly release subcutaneously (see Rao, *J. Biomater Sci. Polym. Ed.* 7:623-645, 1995); as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The beta-blocker pharmaceutical formulations of the invention may be provided as a salt and may be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, a preparation may be a lyophilized powder that is combined with buffer prior to use.

The beta-blocker formulations of the invention may be useful for parenteral administration, such as intravenous (IV) administration. The formulations for administration may include a solution of the beta-blocker dissolved in a pharmaceutically acceptable carrier. Among the acceptable vehicles and solvents that may be employed, include, but are not limited to, water and Ringer's solution, an isotonic sodium chloride, etc. In addition, sterile fixed oils may conventionally be employed as a solvent or suspending medium. For this purpose any bland fixed oil may be employed including synthetic mono- or diglycerides. In addition, fatty acids such as oleic acid can likewise be used in the preparation of injectables. Accordingly, the beta-blocker agent(s) may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of beta-blockers in these formulations may vary widely, and will be selected based on fluid volumes, viscosities, body weight, and the like, in accordance with the particular mode of administration selected and the patient's needs. For IV administration, the formulation may be a sterile injectable preparation, such as a sterile injectable aqueous or oleaginous suspension. This suspension may be formulated according to the known art using those suitable dispersing or wetting agents and-suspending agents. The sterile injectable preparation may also be a sterile injectable solution or suspension in a nontoxic parenterally-acceptable diluent or solvent, such as a solution of 1,3-butanediol, and the like. Accordingly, beta-blocker formulations suitable for parenteral administration may include sterile aqueous and non-aqueous injection solutions of one or more active beta-blocker agents, which preparations may be isotonic with the blood of the intended recipient. These preparations may contain, buffers and solutes which render the formulation isotonic with the blood of the intended recipient. Aqueous and non-aqueous sterile suspensions may include suspending agents and thickening agents. The formulations may be presented in single- or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind described above.

In another embodiment, the beta-blocker formulations of the invention may be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the beta-blocker into the target cells in vivo. (See, e.g., Al-Muhammed, *J. Microencapsul.* 13:293-306, 1996; Chonn, *Curr. Opin. Biotechnol.* 6:698-708, 1995; Ostro, Am. *J. Hosp. Pharm:* 46:1576-1587, 1989). Accordingly, embodiments may include one or more beta-blockers administered as liposomal formulations of the beta-blockers. Methods for preparing liposomal suspensions are known in the art and thus will not be described herein in great detail. Briefly, in those embodiments where the beta-blocker is an aqueous-soluble beta-blocker, the beta-blocker may be incorporated into lipid vesicles using conventional liposome technology. In such instances, due to the water solubility of the beta-blocker, the beta-blocker may be substantially entrained within the hydrophilic center or core of the liposomes. The lipid layer employed may be of any conventional composition and may either contain cholesterol or may be cholesterol-free. When the beta-blocker of interest is water-insoluble, the beta-blocker may be substantially entrained within the hydrophobic lipid bilayer which forms the structure of the liposome employing conventional liposome formation technology. In either instance, the liposomes which may be produced may be reduced in size, as through the use of standard sonication and homogenization techniques. Embodiments of liposomal formulations containing the beta-blocker of interest may be lyophilized to produce a lyophilizate which may be reconstituted with a pharmaceutically acceptable carrier, such as water, to regenerate a liposomal suspension.

As is described in greater detail below, a pharmaceutical composition of the subject invention may optionally contain, in addition to a beta-blocker, at least one other therapeutic agent useful in the treatment of a condition. Such other compounds may be of any class of drug or pharmaceutical agent, including but not limited to antibiotics, anti-parasitic agents, antifungal agents, anti-viral agents, anti-tumor agents, anti-neurodegenerative agents and anti-psychotic agents. When administered with anti-parasitic, anti-bacterial, anti-fungal, anti-tumor, anti-viral agents, anti-neurodegenerative, and anti-psychotic agents and the like, beta-blockers may be administered by any method and route of administration suitable to the treatment of the condition, typically as pharmaceutical compositions.

Embodiments of the one or more beta-blockers employed in the practice of the subject invention may include pharmaceutical beta-blocker compositions that may be prepared from water-insoluble compounds, or salts thereof, such as aqueous base emulsions. In such embodiments, the beta-blocker composition will typically contain a sufficient amount of pharmaceutically acceptable emulsifying agent to emulsify the desired amount of the beta-blocker. Useful emulsifying agents include, but are not limited to, phosphatidyl cholines, lecithin, and the like.

As noted above, in addition to active beta-blocker agents, the pharmaceutical beta-blocker compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Furthermore, beta-blocker compositions may, though not always, contain microbial preservatives. Microbial preservatives that may be employed include, but are not limited to, methylparaben, propylparaben, and benzyl alcohol. The microbial preservative may be employed when the beta-blocker formulation is placed in a vial designed for multidose use. Pharmaceutical beta-blocker compositions for use in practicing the subject methods may be lyophilized using techniques well known in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Embodiments may also include administration of at least one beta-blocker using a pharmacological delivery device such as, but not limited to, pumps (implantable or external devices), epidural injectors, syringes or other injection apparatus, catheter and/or reservoir operatively associated with a catheter, etc. For example, in certain embodiments a delivery device employed to deliver at least one beta-blocker to a subject may be a pump, syringe, catheter or reservoir operably associated with a connecting device such as a catheter, tubing, or the like. Containers suitable for delivery of at least one beta-blocker to a beta-blocker administration device include instruments of containment that may be used to deliver, place, attach, and/or insert the at least one beta-blocker into the delivery device for administration of the beta-blocker to a subject and include, but are not limited to, vials, ampules, tubes, capsules, bottles, syringes and bags.

In certain embodiments, the pharmaceutically acceptable carrier is preservative free. By "preservative free" is meant the substantial absence of chemical, antibacterial, antimicrobial, or antioxidative additives, or the like, from the pharmaceutically acceptable carriers of the present invention. "Substantial absence" may mean that no preservative is present in the compositions or that trace amounts may be present that impart no detectable effect otherwise attributable to a preservative. For example, the pharmaceutically acceptable carrier may be characterized by the substantial absence of chemical, antibacterial, antimicrobial, or antioxidative additives or the like (e.g., contain less than about 5.0, 4.0, 3.0, 2.0, 1.0, 0.5, 0.1, 0.05, 0.01, or even about 0.00 percent by weight of a preservative). Further, such formulations may be substantially or essentially free of alcohols such as ethanol (e.g., contain less than about 5.0, 4.0, 3.0, 2.0, 1.0, 0.5, 0.1, 0.05, 0.01, or even about 0.00 percent by weight of alcohols such as ethanol). Examples of suitable beta-blocker formulations include, but are not limited to, formulations that include one or more active beta-blocker agents and physiological saline solution (optionally including other typical ingredients such as other active agents and buffers).

As noted above, in pharmaceutical dosage forms, the agents may be administered alone or with or in appropriate association, as well as in combination, with other pharmaceutically active compounds. As used herein, "administered with" means that at least one beta-blocker and at least one other adjuvant (including one or more other beta-blockers) are administered at times sufficiently close that the results observed are indistinguishable from those achieved when at least one beta-blocker and at least one other adjuvant are administered at the same point in time. The at least one beta-blocker and at least one other adjuvant may be administered simultaneously (i.e., concurrently) or sequentially. Simultaneous administration may be carried out by mixing the at least one beta-blocker and at least one other adjuvant prior to administration, or by administering the at least one beta-blocker and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that the at least one beta-blocker and at least one other adjuvant are administered at the same point in time or immediately following one another. In the latter case, the at least one beta-blocker and at least one other adjuvant are administered at times sufficiently close that the results produced are synergistic and/or are indistinguishable from those achieved when the at least one beta-blocker and at least one other adjuvant are administered at the same point in time. Alternatively, a beta-blocker may be administered separately from the administration of an adjuvant, which may result in a synergistic effect or a separate effect. The methods and excipients described herein are merely exemplary and are in no way limiting.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous or other suitable administration route may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent(s) of the present invention calculated in an amount sufficient to produce the desired effect in association with a pharmaceutically acceptable diluent, carrier or vehicle. The specifications for the unit dosage forms of beta-blockers of the present invention depend on, for example, the particular beta-blocker(s) employed and the effect to be achieved, the pharmacodynamics associated with the particular beta-blocker(s) in the subject, etc.

As noted above, those of skill in the art will readily appreciate that dose levels may vary as a function of the specific pharmacological beta-blocker agent(s), the nature of the delivery vehicle, and the like. Dosages for a given pharmacological beta-blocker agent(s) are readily determinable by those of skill in the art by a variety of means. Exemplary dosage levels are provided herein are not to be construed to limit the scope of the invention in any manner.

Introduction of an effective amount of at least one beta-blocker agent to a subject as described above results in a modulation of at least a portion of the autonomic nervous system, where the modulation may be temporary or permanent. More specifically, administration of an effective amount of at least one beta-blocker agent to a subject at least results in a temporary or permanent decrease, reduction or inhibition in activity of at least a portion of the sympathetic nervous system.

A wide variety of different beta-blockers may be employed in the practice of the subject methods, where the particular beta-blocker or combination of beta-blockers employed will depend on, e.g., the subject being treated, the condition being treated, duration of treatment, etc. Representative beta-blockers include, but are not limited to, atenolol (e.g., as sold under the brand names TENORMIN), betaxolol (e.g., as sold under the brand name KERLONE), bisoprolol (e.g., as sold under the brand name ZEBETA), carvedilol (e.g., as sold under the brand name COREG), esmolol (e.g., as sold under the brand name BREVIBLOC), labetalol (e.g., as sold under the brand name NORMODYNE), metoprolol (e.g., as sold under the brand name LOPRESSOR), nadolol (e.g., as sold under the brand name CORGARD), pindolol (e.g., as sold under the brand name VISKEN), propranolol (e.g., as sold under the brand name INDERAL), sotalol (e.g., as sold under the brand name BETAPACE), timolol (e.g., as sold under the brand name BLOCADREN), carvedilol, and the like, and combinations thereof.

As noted above, embodiments include administering an effective amount of at least one beta-blocker and an effective amount of at least one non-beta-blocker, e.g., concurrently administered. A wide variety of different non-beta-blocker pharmacological agents may be employed in the practice of the subject methods, in addition to the administration of at least one beta-blocker, where the particular additional pharmacological agent(s) employed may be, but are not limited to, analgesics (e.g., acetaminophen (e.g., available under the brand name TYLENOL), non-steroidal anti-inflammatory drugs such as naproxen (e.g., available under the brand name ALLEVE), ibuprofen (e.g., available under the brand names ADVIL, MOTRIN), and the like), antiinflammatories, etc., where in certain embodiments the non-beta-blocker agent(s) may assist in modulating the autonomic nervous system to treat the condition of interest. For example, embodiments may include administering a beta-blocker and at least one non-beta-blocker agent to provide an enhanced therapeutic effect. By "enhanced therapeutic effect" is meant that at least the initial relief of the particular condition being treated by the particular beta-blocker employed occurs more quickly with a combination of the beta-blocker and at least one other pharmacological agent such as at least one other non-beta-blocker pharmacological agent, as compared to the same doses of each component given alone; or that doses of one or all component(s) (the beta-blocker and at least one other pharmacological agent such as at least one other non-beta-blocker pharmacological agent) are below what would otherwise be a minimum effective dose (a "sub-MED").

Accordingly, the subject invention includes treating a subject for a condition by modulating at least a portion of the subject's autonomic nervous system by administering at least one beta-blocker together with at least one other pharmacological agent such together with as at least one other non-beta-blocker pharmacological agent. The at least one beta-blocker and at least one non-beta-blocker agent may be concomitantly administered as described above, i.e., they may be given in close enough temporal proximity to allow their individual therapeutic effects to overlap. For example, embodiments of the subject invention include the co-timely administration of a beta-blocker and a non-beta-blocker. By "co-timely" with respect to drug administration is meant administration of a second pharmacological agent (e.g., a non-beta-blocker agent) for the treatment of a condition while a first pharmacological agent (e.g., a beta-blocker) is still present in a therapeutically effective amount. It is to be understood that in some instances this will require sequential administration. Alternatively, multiple routes of administration may be employed, e.g., intravenous or subcutaneous injection of a beta-blocker may be combined with oral administration of a non-beta-blocker agent.

Embodiments also include pharmaceutical compositions in unit dosage forms that are useful in treating conditions by modulating at least a portion of a subject's autonomic nervous system and which contain a beta-blocker agent and a non-beta-blocker agent. In other words, a single drug administration entity may include two or more pharmacological agents, e.g., a single drug administration entity may include at least one beta-blocker and at least one non-beta-blocker. For example, a single tablet, capsule, dragee, trocheem suppository, syringe, and the like, combining two or more pharmacological agents, e.g., a single drug administration entity may include at least one beta-blocker and at least one non-beta-blocker, would be a unit dosage form. The therapeutic agents present in a unit dosage form are typically present in amounts such that, upon administration of one or more unit doses of the composition, a subject experiences a longer lasting efficacy than with the administration of either agent alone. Such compositions may be included as part of a therapeutic package in which one or more unit doses are placed in a finished pharmaceutical container. Labeling may be included to provide directions for using the composition in the treatment of a condition by modulating at least a portion of a subject's autonomic nervous system. The actual amounts of each agent in such beta-blocker/non-beta-blocker compositions will vary according to the specific compositions being utilized, the particular compositions formulated, the mode of application, the particular route of administration, and the like. Dosages for a given subject can be determined using conventional considerations, e.g., by customary comparison of the differential activities of the subject compositions and of a known agent, or by means of an appropriate, conventional pharmacological protocol. A person of ordinary skill in the art will be able without undue experimentation, having regard to that skill and this disclosure, to determine a therapeutically effective amount of a particular non-beta-blocker agent for practice of this invention. For example, embodiments may include dosages conventionally administered for the particular non-beta-blocker employed, where such dosages are known in the art.

The particular non-beta-blocker agent(s) employed will depend on the subject being treated, the condition being treated, the at least one beta-blocker employed, whether it is desired to increase activity in the parasympathetic system and/or decrease activity in the sympathetic system, etc. Exemplary, representative non beta-blocker pharmacological agents that may be employed in the practice of the subject invention include, but are not limited to: aldosterone antagonists (e.g., spironolactone, eplerenone, and the like); angiotensin II receptor blockades (e.g., candeartan (e.g., available under the brand name ALTACAND), eprosarten mesylate (e.g., available under the brand name TEVETAN), irbesartan (e.g., available under the brand name AVAPRO), losartan (e.g., available under the brand name COZAAR), etelmisartin (e.g., available under the brand name MICARDIS), valsartan (e.g., available under the brand name DIOVAN), and the like); angiotensin converting enzyme inhibitors (e.g., benazapril (e.g., available under the brand name LOTENSIN), captopril (e.g., available under the brand name CAPOTEN) enalapril (e.g., available under the brand name VASOTEC) fosinopril (e.g., available under the brand name MONOPRIL) lisinopril (e.g., available under the brand name PRINIVIL) moexipril (e.g., available under the brand name UNIVASC) quinapril (e.g., available under the brand name ACCUPRIL) ramipril (e.g., available under the brand name ALTACE) trandolapril (e.g., available under the brand name MAVIK), and the like); statins (e.g., atorvastatin (e.g., available under the brand name LIPITOR), cerivastatin (e.g., available under the brand name BAYCOL), fluvastatin (e.g., available under the brand name LLESCOL), lovastatin (e.g., available under the brand name MEVACOR), prevastatin (e.g., available under the brand name PRAVACHOL), simvastatin (e.g., available under the brand name ZOCOR), and the like); triglycerides lowering drugs (e.g., fenofibrate (e.g., available under the brand name TRICOR), genfibrozil (e.g., available under the brand name LOPID), and the like); niacin; anti-diabetes agents (e.g., acarbose (e.g., available under the brand name PRECOSE), glimepiride (e.g., available under the brand name AMA-RYL), glyburide (e.g., available under the brand names MICRONASE, DIABETA), metformin (e.g., available under the brand name GLUCOPHASGE), miglitol (e.g., available under the brand name GLYCET), pioglitazone (e.g., available under the brand name ACTOS), repaglinide (e.g., available under the brand name PRANDIN), rosiglitazone (e.g., available under the brand name AVANDIA), and the like); immunomodulators (e.g., interferon beta-1B (e.g., available under the brand name BETASERON), interferon alfa-2A (e.g., available under the brand name ROFERON-A) interferon alfa-2B (e.g., available under the brand name INTRON-A), interferon alfa-2Band Ribavirin combo pack (e.g., available under the brand name REBETRON), interferon alfa-N3 (e.g., available under the brand name ALFERON N), interferon beta-1A (e.g., available under the brand name AVONEX), interferon gamma immunoregulatory antibodies that bind to or react with one of the following antigens: CD4, gp39, B7, CD19, CD20, CD22, CD401, CD40, CD40L and CD23, rituximab (e.g., available under the brand name RITUXAN), any chemical or radiopharmaceutical linked or conjugated antibodies that bind to or react with one of the following antigens: CD4, gp39, B7, CD19, CD20, CD22, CD401, CD40, CD40L and CD23), and the like); nicotine; sympathomimetics (e.g., trimethaphan, clondine, reserpine, guanethidine, and the like); antihistamines (e.g., available under the brand name BENADRYL, diphenhydramine, available under the brand name ACTIFED, and the like); cholinergics (e.g., bethanechol, oxotremorine, methacoline, cevimeline, and the like); acetylcholinesterase inhibitors (e.g., edrophonium, neostigmine, donepezil, tacrine, echothiophate, diisopropylfluorophosphate, demecarium, pralidoxime, galanthamine, tetraethyl pyrophosphate, parathoin, malathion, isoflurophate, metrifonate, physostigmine, rivastigmine, abenonium acetylchol, carbaryl acetylchol, propoxur acetylchol, aldicarb acetylchol, and the like); magnesium and magnesium sulfates; calcium channel blockers (e.g., amlodipine besylate (e.g., available under the brand name NORVASC), diltiazem hydrochloride (e.g., available under the brand names CARDIZEM CD, CARDIZEM SR, DILACOR XR, TIAZAC), felodipine plendil isradipine (e.g., available under the brand names DYNACIRC, DYNACIRC CR), nicardipine (e.g., available under the brand name CARDENE SR), nifedipine (e.g., available under the brand names ADALAT CC, PROCARDIA XL), nisoldipine (e.g., available under the brand name SULAR), verapamil hydrochloride (e.g., available under the brand names CALAN SR, COVERA HS, ISOPTIN SR, VERELAN) and the like); muscarinics (e.g., muscarine, pilocarpine, and the like); sodium channel blockers, (e.g., moricizine, propafenone, encainide, flecainide, tocainide, mexiletine, phenytoin, lidocaine, disopyramide, quinidine, procainamide, and the like); glucocorticoid receptor blockers (e.g., mifepristone, and the like); peripheral andrenergic inhibitors (e.g., guanadrel (e.g., available under the brand name HYLOREL), guanethidine monosulfate (e.g., available under the brand name ISMELIN), reserpine (e.g., available under the brand names SERPASIL, MECAMYLAMINE, HEXEMETHONIUM), and the like); blood vessel dilators (e.g., hydralazine hydrocholoride (e.g., available under the brand name APRESOLINE), minoxidil (e.g., e.g., available under the brand name LONITEN), and the like); central agonists (e.g., alpha methyldopa (e.g., available under the brand name ALDOMET), clonidine hydrochloride (e.g., available under the brand name CATAPRES), guanabenz acetate (e.g., available under the brand name WYTENSIN), guanfacine hydrochloride (e.g., available under the brand name TENEX), and the like; combined alpha and beta-blockers (e.g., carvedilol (e.g., available under the brand name COREG), labetolol hydrochloride (e.g., available under the brand names NORMODYNE, TRANDATE), and the like); alpha blockers (e.g., doxazosin mesylate (e.g., available under the brand name CARDURA), prazosin hydrochloride (e.g., available under the brand name MINIPRESS), terazosin hydrochloride (e.g., available under the brand name HYTRIN), and the like); combination diuretics (e.g., amiloride hydrochloride+hydrochlorothiazide (e.g., available under the brand name MODURETIC), spironolactone+hydrochlorothiazide (e.g., Aldactazide), triamterene+hydrochlorothiazide (e.g., available under the brand names DYAZIDE, MAXZIDE) and the like); potassium sparing diuretics (e.g., amiloride hydrochloride (e.g., available under the brand name MIDAMAR), spironolactone (e.g., available under the brand name ALDACTONE), triamterene (e.g., available under the brand name DYRENIUM), and the like); nitrates (e.g., L-arginine, (e.g., available under the brand names NITROGLYCERIN DEPONIT, MINITRAN, NITROPAR, NITROCINE, NITRO-DERM, NITRO DISC, NITRO-DUR, NITROGARD, NITROGLYCERIN, NITROGLYCERIN T/R, NITRO-TIME, NITROL OINTMENT, NITROLINGUAL SPRAY, NITRONG, NITRO-BID, NITROPRESS, NITROPREX, NITRO S.A., NITROSPAN, NITROSTAT, NITRO-TRANS SYSTEM, NITRO-TRANSDERMAL, NITRO-TIME, TRANSDERM-NITRO, TRIDIL. PENTAERYTHRITOL TETRANITRATE PERITRATE, PERITRATE S.A. ERYTHRITYL TETRANITRATE CARDILATE ISOSORBIDE DINITRATE/PHENOBARBITAL ISORDIL W/PB ISOSORBIDE MONONITRATE IMDUR, ISMO, ISOSORBIDE MONONITRATE, MONOKET ISOSORBIDE NITRATE DILATRATE-SR, ISO-BID, ISORDIL, ISORDIL TEMBIDS, ISORDIL DINITRATE, ISORDIL DINITRATE LA, SORBITRATE, SORBITRATE SA), and the like); cyclic nucleotide monophodiesterase ("PDE") inhibitors (e.g., vardenafil (e.g., available under the brand name LEVITRA), sildenafil (e.g., available under the brand name VIAGRA) tadalafil (e.g., available under the brand name CIALIS) and the like); alcohols; catecholamines inhibitors; neurotoxins, (e.g., botox and capsaicin (e.g., delivered locally, to disable sympathetic function) and the like); vasopressin inhibitors (e.g., atosiban, and the like); oxytocin inhibitors; relaxin hormone; renin inhibitors (e.g., Aliskiren, and the like); estrogen and analogues (e.g., estradiols, and the like) and metabolites; progesterone inhibitors; testosterone inhibitors; gonadotropin-releasing hormone analogues (GnRH-As); gonadotropin-releasing hormone inhibitors (e.g., Leuprolide Acetate, and the like); vesicular monoamine transport (VMAT) inhibitors (e.g., tetrabenazine, and the like); dipeptidyl peptidase (DP) IV inhibitors (DP4 inhibitors) (e.g., LAF237, P93/01, P32/98, valine pyrrolidide, and the like); melatonin; and combinations thereof.

Accordingly, in practicing the subject methods, an effective amount of at least one beta-blocker is administered to a subject to treat a condition affecting the subject. As noted above, the particular dosage, mode of administration, treatment times, etc., will vary according to a variety of factors, but will generally fall within the ranges provided above.

For example, embodiments include modulating sympathetic activity by administration of an effective amount of atenolol. Such embodiments may include administering a beta-blocker such as atenolol orally, e.g., in the form of an extended-release capsule or tablet. In those embodiments that include administering an effective amount of a beta-blocker, e.g., atenolol, orally by extended-release capsule or tablet, typically, though not always, the capsule or tablet is administered whole, i.e., not crushed, broken or chewed before swallowing. In those embodiments that include administering an effective amount of a beta-blocker such as propranolol orally by oral solution of propranolol, the oral solution is administered by mouth and may be taken or mixed with a liquid such as water, juice, carbonated rink, etc. or other food or drink product such as applesauce, pudding, etc.

As noted above, the dose of beta-blocker will be different for different subject, conditions treated, etc. The following embodiments describe average doses and may vary. Such are for exemplary purposes only and are in no way intended to limit the scope of the invention. For example, the number of capsules or tablets, teaspoonfuls of solution, and the like, administered depends at least in part on the strength of the particular beta-blocker administered. Furthermore, the number of doses administered each day, the time allowed between doses, and the length of time a subject takes the medicine, etc., depend on the condition being treated, i.e., the condition for which a subject is taking the beta-blocker.

As noted above, embodiments may include administering an effective amount of acebutolol to treat a condition. Such embodiments may include administering oral dosage forms (capsules and tablets) of acebutolol ranging from about 200 milligrams (mgs.) to about 1200 mgs., e.g., from about 200 mgs. to about 800 mgs. Such oral dosages may be administered as a single dose one time a day, two times a day, or divided into two daily doses for an adult, etc.

Embodiments may include administering atenolol to treat a condition. Such embodiments may include administering adult oral dosage forms (e.g., tablets) of atenolol (e.g., available under the brand name TENORMIN) that range from about 25 mgs. to about 100 mgs. once a day. For example, administration may include about 50 mgs. once a day, or about 100 mgs. of atenolol once a day, or about 50 mgs. atenolol two times a day, e.g., for about six to about nine days. Embodiments that include administering atenolol in adult injection dosage forms may include about 5 mgs. given over 5 minutes, repeated ten minutes later.

Embodiments may include administering adult oral dosage forms (e.g., tablets) of betaxolol to treat a condition. Such embodiments may include administering about 10 mgs. of betaxolol as an adult dosage form once a day.

Embodiments may include administering adult oral dosage forms (e.g., tablets) of bisoprolol (e.g., available under the brand name ZEBETA) to treat a condition. Such embodiments may include administering about 5 mgs. to about 10 mgs. of bisoprolol as an adult oral dosage forms (e.g., tablets) once a day.

Embodiments may include administering adult oral dosage forms (e.g., tablets) of carteolol to treat a condition. Adult oral dosage forms (e.g., tablets) of carteolol may include about 0.5 mgs. to about 10 mgs. once a day.

Embodiments may include administering adult oral dosage forms (e.g., tablets) of labetalol to treat a condition. Adult oral dosage forms (e.g., tablets) of labetalol may include about 100 mgs. to about 400 mgs. two times a day. Adult injection dosage forms may include about 20 mgs., e.g., injected slowly over about two minutes with additional injections of about 40 mgs. and about 80 mgs. given about every ten minutes if needed, up to a total of about 300 mgs., instead as an infusion at a rate of about 2 mgs. per minute to a total dose of about 50 mgs. to about 300 mgs.

Embodiments may include administering adult oral dosage forms (e.g., tablets) of metaprolol to treat a condition. Adult oral dosage forms (e.g., tablets) of metoprolol may include about 100 mgs. to 450 mgs. a day, taken as a single dose or in divided doses. For example, embodiments may include administering about 50 mgs. about every six hours for about 24 hours or more and then about 100 mgs. two times a day for about 1 to about 3 months or more, e.g., from about 1 to about 3 years or more. Embodiments may include administering long-acting adult oral dosage forms (extended-release tablets) that may include up to about 400 mgs. once a day. Adult injection dosage form may include about 5 mgs. every two minutes for about three doses.

Embodiments may include administering adult oral dosage forms (e.g., tablets) of nadolol (e.g., available under the brand name CORGARD) to treat a condition. Embodiments ay include administering adult oral dosage forms (e.g., tablets) of nadolol that may include about 40 mgs. to about 320 mgs. once a day.

Embodiments may include administering adult oral dosage forms (e.g., tablets) of oxprenolol to treat a condition. Embodiments may include administering adult oral dosage forms (e.g., tablets) of oxprenolol (short-acting) that may include about 20 mgs. three times a day. Embodiments may include administering adult long-acting oral dosage forms (extended-release tablets) that may include about 120 mgs. to about 320 mgs. once a day.

Embodiments may include administering adult oral dosage forms (e.g., tablets) of pentbutolol to treat a condition. Embodiments may include administering adult oral dosage forms (e.g., tablets) of penbutolol that may include about 20 mgs. once a day.

Embodiments may include administering adult oral dosage forms (e.g., tablets) of pindolol to treat a condition. Embodiments may include administering adult oral dosage forms (e.g., tablets) of pindolol that may include about 5 mgs. two times a day—up to about 60 mgs. a day.

Embodiments may include administering adult oral dosage forms (e.g., tablets) of propranolol to treat a condition. Embodiments may include administering adult oral dosage forms (e.g., tablets) of propranolol that may include, for regular (short-acting) oral dosage forms (tablets and oral solution), about 80 mgs. to about 320 mgs. a day taken in two, three, or four divided doses up to about 640 mgs./day in certain embodiments. Embodiments may also include about 10 mgs. to about 40 mgs. three or four times a day for an adult and about 500 micrograms (0.5 mgs.) to about 4 mgs. per kilogram of body weight a day taken in divided doses for children. Embodiments may include administering long-acting adult oral dosage forms (extended-release capsules) that may include about 80 mgs. to about 320 mgs. once a day up to about 640 mgs. once a day. Embodiments may include administering adult injection dosage forms that range from about 1 mg. to about 3 mgs. given at a rate not greater than about 1 mg per minute. The dose may be repeated after about two minutes and again after about four hours if needed. Children may be administered about 10 mgs. to about 100 micrograms (0.01 to 0.1 mg) per kilogram of body weight given intravenously about every six to eight hours.

Embodiments may include administering adult oral dosage forms (e.g., tablets) of sotalol to treat a condition. Embodiments may include administering adult oral dosage forms (e.g., tablets) of sotalol that may include about 80 mgs. two times a day up to about 320 mgs. per day taken in two or three divided doses.

Embodiments may include administering adult oral dosage forms (e.g., tablets) of timolol (e.g., available under the brand name BLOCADREN) to treat a condition. Embodiments may include administering adult oral dosage forms (e.g., tablets) of timolol that may include about 10 mgs. two times a day up to about 60 mgs. per day taken as a single dose or in divided doses. For example, up to 30 mgs. once a day or in divided doses.

As noted above, in addition to an effective amount of at least one beta-blocker, an effective amount of at least one non beta-blocker agent may also be administered to a subject to treat a condition. As noted above, the dose of non beta-blocker will be different for different subject, conditions treated, etc. The following embodiments describe average doses of various non beta-blocker agents that may be employed in the practice of the subject invention and may vary. Such are for exemplary purposes only and are in no way intended to limit the scope of the invention. For example, the number of capsules or tablets, teaspoonfuls of solution, and the like, administered depends at least in part on the strength of the particular non beta-blocker administered. Furthermore, the number of doses administered each day, the time allowed between doses, and the length of time a subject takes the medicine, etc., depend on the condition being treated, i.e., the condition for which a subject is taking the non beta-blocker. A person of ordinary skill in the art will be able without undue experimentation, having regard to that skill and this disclosure, to determine a therapeutically effective amount of a particular non beta-blocker agent for practice of this invention. For example, embodiments may include dosages conventionally administered for the particular non beta-blocker employed, where such dosages are known in the art.

Aldosterone Antagonists

Embodiments may include administering an aldosterone antagonist to treat a condition in accordance with the subject invention. For example, embodiments may include administering adult oral dosage forms (e.g., tablets) of spironolactone that may range from about 50 mgs. to about 400 mgs. daily. Embodiments may include administering adult oral dosage forms (e.g., tablets) of eplerenone that may range from about 50 mgs. to about 100 mgs. daily.

Angiotensin II Receptor Blockades

Embodiments may include administering an angiotensin II receptor blockade to treat a condition in accordance with the subject invention. Such embodiments may include administering an adult oral dosage form of candesartan (e.g., ATACAND) to a subject to treat a condition. Exemplary treatment protocols may include administering about 2 mgs. to about 32 mgs. of candesarten daily (i.e., for a 24 hour interval), e.g., about 16 mgs. daily. Embodiments may include administering adult oral dosage forms of irbersarten (e.g., AVAPRO) to a subject to treat a condition. Exemplary treatment protocols may include administering about 75 mgs. to about 100 mgs. or more, e.g., up to about 300 mgs., of irbersarten daily. Embodiments may include administering adult oral dosage forms of losarten (e.g., COZAAR) to a subject to treat a condition. Exemplary treatment protocols may include administering about 25 mgs. to about 50 mgs. or more, e.g., 100 milligrams, of losarten orally once daily or twice daily. Embodiments may include administering adult oral dosage forms of telmisartin (e.g., MICARDIS) to a subject to treat a condition. Exemplary treatment protocols may include administering about 20 mgs. to about 80 mgs. of telmisartin daily. Embodiments may include administering adult oral dosage forms of valsartan (e.g., DIOVAN) to a subject to treat a condition. Exemplary treatment protocols may include administering about 20 mgs. to about 80 mgs. of valsarten once daily. Embodiments may include administering adult oral dosage forms of eprosarten (e.g., TEVETAN) to a subject to treat a condition. Exemplary treatment protocols may include administering about 400 mgs. to about 800 mgs. of eprosarten once daily or twice daily.

Angiotensin Converting Enzyme Inhibitors (ACE Inhibitors)

Embodiments may include administering an ACE inhibitor to a subject to treat a condition in accordance with the subject invention. Such may include administering adult oral dosage forms of captropil (e.g., CAPOTEN) to a subject to treat a condition. Exemplary treatment protocols may include administering about 12.5 mgs. to about 50 mgs. of captropil over about 8 to about 12 hours. Embodiments may include administering adult oral dosage forms of enalapril (e.g., VASOTEC) to a subject to treat a condition. Exemplary treatment protocols may include administering about 5 mgs. to about 20 mgs. of enalapril once daily. Embodiments may include administering adult oral dosage forms of fosinopril (e.g., MONOPRIL) to a subject to treat a condition. Exemplary treatment protocols may include administering about 10 mgs. to about 80 mgs., e.g., about 20 mgs. to about 40 mgs., of fosinopril daily. Embodiments may include administering adult oral dosage forms of lisinopril (e.g., PRINIVIL) to a subject to treat a condition. Exemplary treatment protocols may include administering about 10 mgs. to about 80 mgs., e.g., about 20 mgs. to about 40 mgs., of lisinopril daily. Embodiments may include administering adult oral dosage forms of moexipril (e.g., UNIVASC) to a subject to treat a condition. Exemplary treatment protocols may include administering about 3.75 mgs. to about 15 mgs., e.g., 7.5 mgs. of moexipril daily. Embodiments may include administering adult oral dosage forms of quinaapril (e.g., ACCUPRIL) to a subject to treat a condition. Exemplary treatment protocols may include administering about 10 mgs. to about 80 mgs, e.g., about 20 mgs., of quinapril once daily. Embodiments may include administering adult oral dosage forms of ramipril (e.g., ALTACE) to a subject to treat a condition. Exemplary treatment protocols may include administering about 2.5 mgs. to about 20 mgs. of ramipril daily. Embodiments may include administering adult oral dosage forms of trandolapril (e.g., MAVIK) to a subject to treat a condition. Exemplary treatment protocols may include administering about 1 mg. to about 4 mgs., e.g., about 2 mgs., of trandolapril daily.

Statins

Embodiments may include administering adult oral dosage forms (e.g., tablets) of a statin to treat a condition in accordance with the subject invention. For example, embodiments may include administering adult oral dosage forms (e.g., tablets) of atorvastatin (e.g., available under the brand name Lipitor) that may range from about 0.5 mgs. to about 80 mgs. daily. Embodiments may include administering adult oral dosage forms (e.g., tablets) of cerivastatin (e.g., available under the brand name Baycol) that may range from about 0.2 mgs. to about 0.3 mgs. daily. Embodiments may include administering adult oral dosage forms (e.g., tablets) of fluvastatin (e.g., available under the brand name lescoL) that may range from about 20 mgs. to about 80 mgs. daily. Embodiments may include administering adult oral dosage forms (e.g., tablets) of lovastatin (e.g., available under the brand name Mevacor) that may range from about 10 mgs. to about 80 mgs. daily. Embodiments may include administering adult oral dosage forms (e.g., tablets) of prevastatin (e.g., available under the brand name Pravachol) that may range from about 10 mgs. to about 40 mgs. daily. Embodiments may include administering adult oral dosage forms (e.g., tablets) of simvastatin (e.g., available under the brand name Zocor) that may range from about 5 mgs. to about 40 mgs. daily.

Triglycerides Lowering Drugs

Embodiments may include administering adult oral dosage forms (e.g., tablets) of a triglycerides lowering drug to treat a condition in accordance with the subject invention. For example, embodiments may include administering adult oral dosage forms (e.g., tablets) of fenofibrate (e.g., available under the brand name TRICOR) that may range from about 65 mgs. to about 200 mgs. daily. Embodiments may include administering adult oral dosage forms (e.g., tablets) of genfibrozil (e.g., available under the brand name LOPID) that may range from about 1200 mgs. total given as about 600 mgs. two times per day (e.g., every 12 hours).

Niacin

Embodiments may include administering niacin to treat a condition in accordance with the subject invention. For example, dosing may include administering by mouth about 2 mgs. to about 6 mgs. total, e.g., as given as about 1 mg. to about 2 mgs. twice per day or three times per day.

Anti-Diabetes Agents

Embodiments may include administering an anti-diabetes drug to treat a condition in accordance with the subject invention. For example, embodiments may include administering adult oral dosage forms (e.g., tablets) of acarbose (e.g., available under the brand name PRECOSE) that may range from about 25 mgs. to about 300 mgs. for an eight hour interval. Embodiments may include administering adult oral dosage forms (e.g., tablets) of glimepiride (e.g., available under the brand name AMARYL) that may range from about 1 mg. to about 2 mgs. daily. Embodiments may include administering adult oral dosage forms (e.g., tablets) of glyburide (e.g., available under the brand names MICRONASE, DIABETA) that may range from about 1.5 mgs. to about 5 mgs. daily. Embodiments may include administering adult oral dosage forms (e.g., tablets) of metformin (e.g., available under the brand name GLUCOPHASGE) that may range from about 500 mgs. to about 850 mgs. for an 8 to 24 hour interval. Embodiments may include administering adult oral dosage forms (e.g., tablets) of miglitol (e.g., available under the brand name GLYCET) that may range from about 25 mgs. to about 100 mgs. for an 8 hour interval. Embodiments may include administering adult oral dosage forms (e.g., tablets) of pioglitazone (e.g., available under the brand name ACTOS) that may range from about 15 mgs. to about 40 mgs. daily. Embodiments may include administering adult oral dosage forms (e.g., tablets) of repaglinide (e.g., available under the brand name PRANDIN) that may range from about 0.5 mgs. to about 4.0 mgs. 3 times per day. Embodiments may include administering adult oral dosage forms (e.g., tablets) of rosiglitazone (e.g., available under the brand name AVANDIA) that may range from about 4 mgs. to about 8 mgs. daily.

Immunomodulators

Embodiments may include administering an immunomodulator to treat a condition in accordance with the subject invention. For example, embodiments may include administering adult dosage form of interferon beta-1B (e.g., available under the brand name BETASERON), where dosing may include administering about 0.25 mg. subcutaneously every other day. Embodiments may also include administering adult dosage form of interferon alfa-2A (e.g., available under the brand name ROFERON-A), where dosing may include administering about 3 million units to about 36 million units per day IM/SC to about 3 million units to about 36 million units 3 times per week (3 million units (1 ml); 6 million units/ml (3 ml); 0 million units/ml (0.9 ml), 3 ml); 36 million units/ml (1 ml)). Embodiments may also include administering adult dosage form of interferon alfa-2B (e.g., available under the brand name INTRON-A), where dosing may include administering about 1 to about 30 million units/M2 IM/SC three times per week (3 million units (0.5 ml); 5 million units (0.5 ml); 10 million units (1 ml); 25 million units powder for injection: 18 million units and 50 million units). Embodiments may also include administering adult dosage form of interferon alfa-2B and ribavirin combination pack (e.g., available under the brand name REBETRON), where dosing may include administering INTRON A at about 3 million units subcutaneously three times per week and about 500 mgs. to about 600 mgs. of ribavirin twice daily. Embodiments may also include administering adult dosage form of interferon alfa-N3 (e.g., available under the brand name ALFERON N), where dosing may include administering about 250,000 units (0.05 ml) twice weekly (5 million units (1 ml)). Embodiments may also include administering adult dosage form of interferon beta-1A (e.g., available under the brand name AVONEX), where dosing may include administering about 30 micrograms IM once weekly (reconstitute with 1.1 ml of diluent).

Nicotine

Embodiments may include administering nicotine to treat a condition in accordance with the subject invention. For example, embodiments may include administering nicotine in the form of chewing gum, e.g., from about 2 mgs. to about 4 mgs. dosage strength). Embodiments may include administering nicotine as an inhalant (e.g., about 4 mgs. per cartridge), nasal spray (e.g., each actuation of nicotine nasal spray may deliver about 0.5 mgs. nicotine), or as a transdermal system. For example, dosing schedules (mg/day) of nicotine transdermal systems may include a patch duration of about 24 hours and dosing schedule of about 7 mgs. to about 22 mgs. for about 2 to about 6 weeks; a patch duration of about 16 hours and a dosing schedule of about 15 mgs. for about 4 to about 12 weeks. Each dosing schedule may be followed by a reduced dosing schedule.

Sympathomimetics

Embodiments may include administering a sympathomimetic to treat a condition in accordance with the subject invention. For example, embodiments may include administering trimethaphan via an I.V., e.g., about 0.1 mgs. to about 1.0 mgs./minute, up to about 15 mgs. per minute. Embodiments may include orally administering clondine at about 0.1 mgs. to about 2.4 mgs. daily. Embodiments may include orally administering reserpine at about 10 mgs. to about 20 mgs. daily. Embodiments may include orally administering guanethidine at about 10 mgs. to about 50 mgs. daily.

Antihistamines

Embodiments may include administering adult oral dosage forms of an antihistamine to treat a condition in accordance with the subject invention. For example, embodiments may include administering adult oral dosage forms (e.g., tablets) of BENADRYL at about 25 mgs. to about 50 mgs. three to four times daily. Nighttime dosage may include about 50 mgs. at bedtime.

Cholinergics

Embodiments may include administering a cholinergic to treat a condition in accordance with the subject invention. For example, embodiments may include administering bethanechol at about 10 mgs. to about 50 mgs. four times per day or three times per day. Embodiments may include administering methacoline as an inhaled aerosol at about 0.02 to about 25.0 mg/mL. Embodiments may include orally administering about 30 mgs. cevimeline three times per day.

Acetylcholinesterase Inhibitors

Embodiments may include administering an acetylcholinesterase inhibitor to treat a condition in accordance with the subject invention. For example, embodiments may include administering about 0.1 ml. to about 0.8 ml via I.V. edrophonium or about 1 ml. of a 1:20000 solution (0.5 mg.) of neostigmine intramuscularly (IM) or subcutaneously (SC). Embodiments may also include orally administering about 5 mg of donepezil to about 10 mgs./day. Embodiments may also include administering about 1 to about 2 g of pralidoxime, e.g., as an infusion in 100 mL of saline, over about a 15 to 30 minute period, via I.V. About 16 mgs to about 32 mgs. of galanthamine may be administered orally twice per day. Physostigmine may be administered intravenously or intramuscularly e.g., about 0.5 mgs. to about 2 mgs. Rivastigmine may be orally administered, e.g., about 3 mgs. to about 6 mgs. two times per day.

Magnesium and Magnesium Sulfates

Embodiments may include administering magnesium to treat a condition in accordance with the subject invention. For example, a dose may include about 0.3 to about 1.0 meq mg/kg daily via an I.V.

Calcium Channel Blockers

Embodiments may include administering a calcium channel blocker to treat a condition in accordance with the subject invention. Embodiments may include orally administering amlodipine besylate (e.g., available under the brand name NORVASC), e.g., about 5 mgs. to about 20 mgs. daily; diltiazem hydrochloride (e.g., available under the brand names CARDIZEM CD, CARDIZEM SR, DILACOR XR, TIAZAC) at about 30 mgs. to about 360 mgs. four times per day (for example 180 mgs. to about 360 mgs. divided into four times per day); felodipine plendil at about 2.5 mgs. to about 10 mgs. daily; isradipine (e.g., available under the brand names DYNACIRC, DYNACIRC CR) at about 2.5 mgs. daily; nicardipine (e.g., available under the brand name CARDENE SR) at about 20 mgs. to about 40 mgs. three times per day; nifedipine (e.g., available under the brand names ADALAT CC, PROCARDIA XL) at about 10 mgs. three times per day; nisoldipine (e.g., available under the brand name SULAR) at about 10 mgs. to about 20 mgs. daily; and verapamil hydrochloride (e.g., available under the brand names CALAN SR, COVERA HS, ISOPTIN SR, VERELAN) at about 40 mgs. three times per day.

Muscarinics

Embodiments may include administering a muscarinic to treat a condition in accordance with the subject invention. For example, embodiments may include administering about 5 mgs. of pilocarpine by mouth to a subject four times per day, up to about 30 mgs./day.

Sodium Channel Blockers

Embodiments may include administering a sodium channel blocker to treat a condition in accordance with the subject invention. For example, embodiments may include administering about 150 mgs. of propafenone by mouth every 8 hours (450 mgs./day) up to about 300 mgs. every 8 hours (90 mgs./day). Embodiments may also include administering about 50 mgs. to about 100 mgs. of flecainide by mouth about every 12 hours up to about 400 mgs./day. Embodiments may also include administering about 400 mgs. to about 2400 mgs. of tocainide by mouth about every 8 hours. Embodiments may also include administering about 100 mgs. to about 200 mgs. of phenytoin by mouth three times per day. Embodiments may also include administering about 10-30 mgs of about 1% to about 2% lidocaine IM (the maximum individual dosage typically should not exceed about 4.5 mg/kg of body weight and generally the maximum total dose should not exceed about 300 mgs.). Embodiments may also include administering about 150 mgs. to about 300 mgs. of dispoyramide by mouth about every 6 hours to about every 12 hours, up to about 1600 mgs. per day. Embodiments may also include administering quinidine (e.g., available under the brand name QUINAGLUTE) at about two tablets (648 mgs.; 403 mgs. of quinidine base) of QUINAGLUTE by mouth about every 8 hours.

Glucocorticoid Receptor Blockers

Embodiments may include administering a glucocorticoid receptor blocker to treat a condition in accordance with the subject invention. For example, embodiments may include administering mifepristone my mouth at about 400 micrograms to about 600 mgs.

Peripheral Andrenergic Inhibitors

Embodiments may include administering a peripheral andrenergic inhibitor to treat a condition in accordance with the subject invention. For example, embodiments may include administering about 5 mgs. to about 75 mgs. of guanadrel (e.g., available under the brand name HYLOREL) by mouth e.g., about 5 mgs. two times per day, about 20 to about 75 mgs. per day in divided doses. Embodiments may also include administering about 10 mgs. to about 50 mgs.

or more per day of guanethidine monosulfate (e.g., available under the brand name ISMELIN) by mouth. Embodiments may also include administering about 0.05 to about 1.5 mgs. once per day by mouth of reserpine (e.g., available under the brand names SERPASIL, MECAMYLAMINE, HEXEMETHONIUM). Embodiments may also include administering about 2.5 mgs. of mecamylamine two times per day by mouth.

Blood Vessel Dilators

Embodiments may include administering a blood vessel dilator to treat a condition in accordance with the subject invention. For example, embodiments may include administering about 10 mgs. to about 50 mgs. of hydralazine hydrocholoride (e.g., available under the brand name APRESOLINE) by mouth four times a day. Embodiments may also include administering about 5 mgs. to about 40 mgs. of minoxidil (e.g., e.g., available under the brand name LONITEN) by mouth once per day.

Central Agonists

Embodiments may include administering a central agonist to treat a condition in accordance with the subject invention. For example, embodiments may include administering about 250 mgs. of alpha methyldopa (e.g., available under the brand name ALDOMET) by mouth three times per day or about 500 mgs. to about 2 grams per day divided into 2 to 4 doses. Embodiments may also include administering about 0.1 mgs. to about 0.6 mgs. of clonidine hydrochloride (e.g., available under the brand name CATAPRES) by mouth once per day. Embodiments may also include administering about 4 mgs. of guanabenz acetate (e.g., available under the brand name WYTENSIN) by mouth two times per day (up to about 32 mgs. per day). Embodiments may also include administering about 1 mg. to about 3 mgs. of guanfacine hydrochloride (e.g., available under the brand name TENEX) by mouth once per day.

Combined Alpha and Beta-Blockers

Embodiments may include administering a combined alpha and beta-blocker to treat a condition in accordance with the subject invention. For example, embodiments may include administering about 100 mgs. two times per day of labetolol hydrochloride (e.g., available under the brand names NORMODYNE, TRANDATE) by mouth up to about 400 mgs. per day. Embodiments may also include administering about 3.125 mgs. two times per day of carvedilol (e.g., available under the brand name COREG) by mouth up to about 50 mgs. per day.

Alpha Blockers

Embodiments may include administering an alpha and beta-blocker to treat a condition in accordance with the subject invention. For example, embodiments may include administering about 1 mg once per day by mouth of doxazosin mesylate (e.g., available under the brand name CARDURA) up to about 16 mgs. per day. Embodiments may also include administering about 0.5 mgs. by mouth of prazosin hydrochloride (e.g., available under the brand name MINIPRESS) two or three times per day (and may include about 6 to about 15 mgs. per day divided into 2 or 3 doses. Embodiments may also include administering about 1 mg. of terazosin hydrochloride (e.g., available under the brand name HYTRIN) by mouth once per day, up to about 5 mgs. per day.

Combination Diuretics

Embodiments may include administering a combined diurentic to treat a condition in accordance with the subject invention. For example, embodiments may include administering about 1-2 tablets of amiloride hydrochloride+hydrochlorothiazide (e.g., available under the brand name MODURETIC) once per day for tablets containing 5 mgs. of anhydrous amiloride HCl and 50 mgs. of hydrochlorothiazide). Embodiments may also include administering about 25 mgs. to about 50 mgs. once per day by mouth of spironolactone+hydrochlorothiazide (e.g., available under the brand name ALDACTAZIDE). Embodiments may also include administering about 1 to 2 tablets one per day of triamterene+hydrochlorothiazide (e.g., available under the brand names DYAZIDE, MAXZIDE) for tablets containing 25 mgs. hydrochlorothiazide and 37.5 mgs. triaterene.

Potassium Sparing Diuretics

Embodiments may include administering a potassium sparing diuretic to treat a condition in accordance with the subject invention. For example, embodiments may include administering about 5 mgs. to about 20 mgs. by mouth once per day of amiloride hydrochloride (e.g., available under the brand name MIDAMAR). Embodiments may also include administering about 25 mgs. to about 200 mgs. once per day by mouth of spironolactone (e.g., available under the brand name ALDACTONE). Embodiments may also include administering about 1 to 2 tablets once per day of triamterene (e.g., available under the brand name DYRENIUM)) for tablets containing 25 mgs. hydrochlorothiazide and 37.5 mgs. triaterene.

Nitrates

Embodiments may include administering a nitrate to treat a condition in accordance with the subject invention. For example, embodiments may include administering isosorbide dinitrate (e.g., avalaible under the brand name ISODIL) at about 50 to about 40 mgs. orally four times per day or 40 mgs. sustained release orally every 8 to 12 hours. Embodiments may also include administering isosorbide mononitrate (e.g., available under the brand names ISMO, MONOKET) at about 20 mgs. orally two times per day and/or may include administering extended release initially about 30 mgs. to about 60 mgs. orally once per day. Maximum of about 240 mgs./day. Embodiments may also include administering nitroglycerine ointment, e.g., about 0.5 inches q8h and/or about 0.5 to about 2 inches every 4 to 6 hours, maximum 4 inches every 4 to 6 hours (0.5 inches is about 7.5 mgs.). Embodiments may also include administering nitrobid, e.g., orally about 2.5 mgs. to about 9 mgs. 2 to 4 times per day. Embodiments may also include administering a nitroglycerin patch, e.g., one patch each day applied and removed at bedtime.

Cyclic Nucleotide Monophosphodiesterase ("PDE") Inhibitors

Embodiments may include administering a cyclic nucleotide monophosphodiesterase ("PDE") inhibitor to treat a condition in accordance with the subject invention. For example, embodiments may include administering about 5 mgs. to about 20 mgs. once per day of vardenafil (e.g., available under the brand name LEVITRA) by mouth. Embodiments may also include administering about 10 mgs. to about 20 mgs. of tadalafil (e.g., available under the brand name CIALIS) orally once per day. Embodiments may also include administering about 25 mgs. to about 100 mgs. of sildenafil (e.g., available under the brand name VIAGRA) orally once per day.

Alcohols

Embodiments may include administering an alcohol to treat a condition in accordance with the subject invention. For example, embodiments may include administering about 200 mgs. orally four times per day or 0.5 to about 1.0 ml per interspace for subarachnoid injections.

Vasopressin Inhibitors

Embodiments may include administering a vasopressin inhibitor to treat a condition in accordance with the subject invention. For example, embodiments may include administering about up to about 6.75 mg administered via IV of atosiban, e.g., 300 microgrms/min to about 100 micrograms/min IV.

Oxytocin Inhibitors

Embodiments may include administering an oxytoxin inhibitor to treat a condition in accordance with the subject invention. For example, embodiments may include administering about 0.25 to about IM of terbutaline, typically not more than about 0.5 mgs. within a four hour period. Embodiments may also include administering about 50 micrograms per minute IV of ritodrine, maximum dosage of about 300 micrograms per minute.

Relaxin Hormone

Embodiments may include administering a relaxin hormone to treat a condition in accordance with the subject invention. For example, embodiments may include administering 1 to 2 tablets of realxin by mouth three times per day fro tablets pf valerian/ayrvedic passion flower blend (550 mgs.)

Renin Inhibitors

Embodiments may include administering a rennin inhibitor to treat a condition in accordance with the subject invention. For example, embodiments may include administering Aliskiren by mouth at about 2 mgs to about 10 mgs./day.

Estrogen and Analogues (e.g., Estradiols) and Metabolites

Embodiments may include administering estrogen and estrogen analogues and estrogen metabolites to treat a condition in accordance with the subject invention. For example, embodiments may include administering about 10 mgs. three times per day.

Gonadotropin-Releasing Hormone Inhibitors

Embodiments may include administering a gonadotropin-releasing hormone inhibitor to treat a condition in accordance with the subject invention. For example, embodiments may include administering leuprolide acetate at about 65 mgs. SQ (subcutaneous) implant.

Vesicular Monoamine Transport (VMAT) Inhibitors

Embodiments may include administering a VMAT inhibitor to treat a condition in accordance with the subject invention. For example, embodiments may include administering tetrabenazine by mouth at about 150 mgs. to about 200 mgs. once per day. Embodiments may also include administering reserpine at about 50 micrograms to about 500 micrograms one time per day.

Dipeptidyl Peptidase (DP) IV Inhibitors (DP4 Inhibitors)

Embodiments may include administering a DP4 inhibitor to treat a condition in accordance with the subject invention. For example, embodiments may include administering LAF237 by mouth at about 25 mgs. to about 200 mgs. per day.

As noted above, embodiments may include employing an electrode to deliver a one or more beta-blockers to a subject. For example, an electrode may be used that has a small port at its tip which is connected to a reservoir or pump containing at least one beta-blocker. The beta-blocker delivery electrode may be implanted using any suitable technique such as surgical cut down, laproscopy, endoscopy, percutaneous procedure, and the like. In certain embodiments a reservoir or pump may also be implanted in the subject's body. The beta-blocker delivery electrode, or other analogous device, may be controllable such that the amount of beta-blocker agent delivered, the rate at which the beta-blocker may be delivered, and the time period over which the beta-blocker may be delivered, etc., may be controllable and may be adjusted.

The actual area(s) of the sympathetic nervous system that may be inhibited with at least one beta-blocker will vary, and include, but are not limited to, pre- and post ganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be inhibited with a beta-blocker in more than one area of the nerve fiber. Targeted areas of the sympathetic nervous system which may be inhibited or dampened in accordance with the subject invention include, but are not limited to, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion; superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; and the like, or a combination of two or more of the above.

In certain embodiments, the subject methods may also include detecting, monitoring, observing, etc., information related to one or more aspects of the autonomic nervous system such as a physical and/or chemical aspect, e.g., activity, balance, etc., in at least a portion of the autonomic nervous system, e.g., in at least a portion of the sympathetic nervous system, and evaluating this information to determine the state of the autonomic nervous system, e.g., the parasympathetic activity and/or sympathetic activity. Once the state of the autonomic nervous system is determined, it may be evaluated in regards to whether the autonomic nervous system is in an abnormal state or in need of modulation, e.g., whether activity in at least a portion of the sympathetic system needs to be decreased to increase the parasympathetic activity/sympathetic activity ratio such that this analysis may be employed as a "trigger" to providing pharmacological beta-blocker modulation of at least a portion of the autonomic nervous system wherein modulation may not be otherwise performed unless the analysis determined such is necessary.

Accordingly, collecting and evaluating this type of data and relating it to whether sympathetic activity modulation is required may be employed as a "trigger" to pharmacologically modulating at least a portion of the autonomic nervous system (e.g., performed prior to, during or following a pharmacological beta-blocker regime) such that such data may indicate whether, when, etc., pharmacological modulation is required—if at all. For example, in certain embodiments pharmacological modulation of at least a portion of a subject's autonomic nervous system may not performed unless one or more aspects of the autonomic nervous system are detected and indicate such modulation is necessary. Any suitable physical and/or chemical aspect or indicator of the autonomic nervous system may be employed, e.g., conduction, catecholamine levels, heart rate variability ("HRV"), action potentials, QT interval, as well as chronotropic, inotropic, and vasodilator responses. In certain embodiments, detection may include detecting the activity or function of a particular organ or system under the control of the autonomic nervous system such as detecting rennin levels for the digestive system, or analogous input parameter. Any suitable detection means may be employed to detect relevant information about the autonomic nervous system, as will be described below.

In certain embodiments, a control feedback loop is provided. For example, during or following a particular beta-blocker treatment regimen, the sympathetic activity (and/or parasympathetic activity) may be monitored, observed, detected, etc., e.g., by sensing conduction in at least a portion of the sympathetic system by any suitable method. Other methods that may be employed to monitor the autonomic balance include, but are not limited to, neurography, continuous or serial measurements of circulating catecholamine levels, chronotropic, inotropic, and vasodilator responses, heart rate variability ("HRV"), post-ganglionic action potentials, QT interval, and the like (see for example Rang S, Wolf H, Montfrans G A, Karemaker J M. Non-invasive assessment of autonomic cardiovascular control in normal pregnancy and pregnancy-associated hypertensive disorders: a review. J Hypertens 2002; 20 (11):2111-9). For example, a sensor suitable for detecting nerve cell or axon activity that are related to the autonomic nervous system may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. Embodiments include utilizing a feedback system in such a manner that, if the desired decrease in sympathetic activity is not achieved, the same or a different beta-blocker protocol may be administered. In other words, in utilizing such a feedback system, if the desired inhibition in activity or level of sympathetic activity is not achieved, the same or a different protocol for inhibiting activity may be performed. For example, in those instances where a different protocol is performed, one or more of the beta-blocker treatment parameters may be modified, e.g., a different beta-blocker may be employed instead or in addition to a first beta-blocker, the mode of administration may be altered, dosage may be altered, etc.

Certain embodiments include simultaneously monitoring, detecting, observing, etc., (i.e., in "real time") the inhibition in the targeted area or sympathetic activity (and/or parasympathetic activity) such that an effective amount of at least one beta-blocker is administered to a subject and the result at least one sympathetic function is observed and/or monitored, e.g., at least once, continuously or intermittently or periodically and in certain embodiments until the desired inhibition in activity (parasympathetic activity/sympathetic activity balance) is observed or longer. Still further, in many embodiments once the desired autonomic nervous system modulation is achieved by at least inhibiting activity in a portion of the sympathetic nervous system, pharmacological agents, including the same of different beta-blocker(s) or other treatment options (surgery, ablation, etc.,) may be administered or otherwise performed thereafter at least one time and may be for a period of time, e.g., one or more times, to maintain the desired state such that the subject methods may be repeated one or more times. For example, in certain embodiments beta-blockers may be administered for a period of days, weeks, months, or even years in certain embodiments.

As noted above, certain embodiments may include further modulating at least a portion of the autonomic nervous system, i.e., in addition to modulation with at least one beta-blocker. Such additional modulation may include methods for inhibiting activity in at least a portion of the autonomic nervous system (e.g., in at least a portion of the sympathetic system and/or parasympathetic system) and/or stimulating or increasing activity in at least a portion of the autonomic nervous system (e.g., in at least a portion of the sympathetic system and/or parasympathetic system). Suitable methods may employ pharmacological means, electrical means, and the like, depending on the desired result.

For example, inhibiting or down-regulating at least a portion of the sympathetic nervous system and/or parasympathetic system may be accomplished in a number of ways. For example, inhibition or down-regulation of activity may be achieved by surgically isolating an effector structure (i.e., the target of the sympathetic and/or parasympathetic activity) from sympathetic and/or parasympathetic innervation, i.e., surgically isolating an effector structure from one or more sympathetic nerve fibers associated with it and/or from one or more parasympathetic nerve fibers associated with it. Furthermore, sympathetic and/or parasympathetic nerves may be ablated, permanently or reversibly, by employing energy delivery devices or cryotherapy. Certain embodiments may employ cryoablation, thermoablation, microwave energy, focus ultrasound, magnetic fields including internal and external magnetic fields, laser energy, optical energy, radiofrequency energy, and the like. The sympathetic and/or parasympathetic system may also be inhibited or down-regulated or depressed by employing pacing mechanisms such as implantable electrode-based pacing systems, external magnetic-based pacing system, and the like. Certain embodiments may include inhibiting activity in at least a portion of the sympathetic and/or parasympathetic nervous system using transcutaneous electrical nerve stimulation ("TENS") or transmagentic stimulation ("TMS") (see for example George, M. Stimulating the Brain. Sci Amer 2003 September). Still further, as noted above, pharmacological agents such as, but not limited to, neurotoxins may be employed to disable sympathetic function and/or parasympathetic function such that the parasympathetic/sympathetic ratio is increased temporarily or permanently. In any event, activity in at least a portion of the sympathetic system and/or parasympathetic system, e.g., one or more nerve fibers associated with the sympathetic and/or parasympathetic system, may be inhibited by employing methods in addition to the administration of at least one beta-blocker.

In certain embodiments, this inhibition may be achieved by employing an electric energy applying device positioned directly on or about (i.e., adjacent) the targeted area of the sympathetic system and/or parasympathetic system. Accordingly, embodiments may include increasing the parasympathetic activity/sympathetic activity ratio by operatively positioning an electric energy applying device on or about the one or more sympathetic nerve fibers desired to be inhibited and electrostimulating the target nerve fibers. Electric energy applying device suitable for achieving this purpose, and methods of performing autonomic nervous system modulation using such devices are described, e.g., in copending U.S. application Ser. No. 10/661,368, entitled "Treatment of Conditions Through Electrical Modulation of the Autonomic Nervous System", the disclosure of which is herein incorporated by reference. In general, inhibiting sympathetic activity and/or parasympathetic activity using such an electric energy applying device Or analogous device, once an electric energy applying device is positioned in a suitable position on or about one or more targeted sympathetic and/or parasympathetic areas such as one or more sympathetic and/or parasympathetic nerve fibers, an electrical output, impulse or signal is applied for a period of time sufficient to provide the desired inhibition. This period of time will vary depending on the area (e.g., the nerve fiber) being inhibited and the desired degree of inhibition, the condition being treated, etc.

As noted above, certain embodiments may include additional modulation that may include methods for stimulating or increasing activity in at least a portion of the autonomic nervous system (e.g., in at least a portion of the parasympathetic system). Accordingly, in certain embodiments activity in at least a portion of the parasympathetic system may be increased to modulate at least a portion of the autonomic nervous system. For example, any portion of the parasympathetic system, e.g., one or more nerve fibers, may be pharmacologically modulated and/or electrically stimulated to increase parasympathetic activity to provide the desired ratio of parasympathetic/sympathetic activity. In other words, activity in at least a portion of the parasympathetic nervous system may be increased by electrical stimulation such that at least a portion of the parasympathetic nervous system may be "up-regulated".

Increasing activity in at least a portion of the parasympathetic system and decreasing activity in at least a portion of the sympathetic system (e.g., with at least one beta-blocker) may be performed simultaneously or sequentially such that at least a portion of the parasympathetic nervous system may be modulated to increase activity therein prior or subsequent to inhibiting activity in at least a portion of the sympathetic nervous system.

Increasing activity in, or up-regulating, at least a part of the parasympathetic system may be desired in instances where sympathetic activity is higher than parasympathetic activity (i.e., there exists a relative sympathetic bias or dominance) and as such the subject methods may be employed to increase parasympathetic activity to a level above or rather to a level that is greater than sympathetic activity or may be employed to modulate the differential between the parasympathetic-sympathetic systems such that the result of increasing parasympathetic activity may be a sympathetic bias, parasympathetic bias or may be an equalization of the two systems (i.e., the activities of the two systems are approximately equal-including equal), but the difference between the parasympathetic-sympathetic systems may be modulated, e.g., reduced or minimized or increased in certain embodiments. Accordingly, as described above, prior to practicing the subject methods, the parasympathetic system may be high, lower or substantially equal to that of the sympathetic system and the net result of the subject methods, whether they include beta-blocker therapy alone or in combination with one or more additional therapies, may be parasympathetic activity that is higher or above that of sympathetic activity, be parasympathetic activity that is less than or lower than that of sympathetic activity, or be parasympathetic activity that is substantially equal to that of sympathetic activity, where activity levels of interest may in terms of systemic levels or regional levels (i.e., localized). Accordingly, embodiments of the subject methods may include increasing parasympathetic activity above that of sympathetic activity and/or may be employed to modulate (increase or decrease) the differential between the two systems, but in any event is employed to increase the ratio of parasympathetic activity to sympathetic activity.

In certain embodiments, a sympathetic bias or dominance may be the normal state, but the ratio of the two systems may be abnormal in a subject. Furthermore, increasing parasympathetic activity may also be desired in instances where parasympathetic activity is higher than the sympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low). For example, such instances may occur where a subject has normal or above normal parasympathetic function, but also has elevated sympathetic function. Other instances include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low.

Accordingly, embodiments may include increasing activity in at least a portion of the parasympathetic system, e.g., one or more nerve fibers associated with the parasympathetic system, using any suitable methods, such as methods analogous to those described above with respect to inhibiting activity in a portion of the autonomic nervous system, e.g., by pharmacological methods and/or electric energy applying methods. For example, to increase activity in at least one area of the parasympathetic system such as a nerve fiber, an electric energy applying device is operatively positioned directly on or about the one or more parasympathetic nerve fibers to which an increase in activity is desired.

The actual area(s) of the parasympathetic nervous system that may be modulated, e.g., pharmacologically and/or electrically stimulated, will vary, and include, but are not limited to, pre- and post ganglionic nerve fibers, as well as ganglionic structures, efferent and afferent nerve fibers, synapses, etc., and combinations thereof in certain embodiments. In certain embodiments, activity in a given nerve fiber may be modulated, e.g., electrically modulated, in more than one area of the nerve fiber. Targeted areas of the parasympathetic nervous system which may be modulated, e.g., electrically stimulated, in accordance with the subject invention include, but are not limited to, the oculomotor nerve; facial nerve; glossopharyngeal nerve; hypoglossal nerve; trigeminal nerve, vagus nerve including the recurrent laryngeal branches of the vagus nerve, the pharyngeal and superior laryngeal branches of the vagus nerve, the cardiac branches of the vagus nerve, the anterior vagal trunk and the posterior vagal trunk; ciliary ganglion; pterygophalatine ganglion; vidian nerve, pterygopalatine nerve, otic ganglion; chorda tympsubmandibular ganglion; lingual nerve; submandibular ganglion; esophageal plexus; parasympathetic branch from inferior hypogastric plexus to descending colon; rectal plexus and pelvic planchnic nerves, or a combination of two or more of the above. For example, in certain embodiments activity may be increased in at least a portion of the vagus nerve and/or to the hypoglossal nerve and/or to the trigeminal nerve.

Certain embodiments may include providing long-term potentiation ("LTP") of at least a portion of the parasympathetic nervous system. LTP may be characterized as an enduring increase in synaptic efficacy resulting from high-frequency stimulation of an afferent (input) pathway. For example, long-term high frequency stimulation of at least a portion of the parasympathetic system may be employed to achieve parasympathetic bias or dominance. More specifically, rapid, intense electrical stimulation of presynaptic neurons associated with the parasympathetic system may be employed to evoke action potentials in one or more postsynaptic neurons such that over time these synapses become increasingly sensitive. This constant level of presynaptic stimulation eventually becomes converted into a larger postsynaptic output which may last for minutes, hours, days, even weeks or more.

The above-described methods find use in a variety of different applications, representative types of which are described in greater detail below.

Utility

The subject methods find use in a variety of applications in which it is desired to treat a subject for a condition caused by, affected or otherwise influences by an abnormality in the subject's autonomic nervous system. In such methods, at least a portion of a subject's autonomic nervous system is pharmacologically modulated with at least one beta-blocker to decrease sympathetic function in at least a portion of the sympathetic nervous system, e.g., to increase the parasympathetic activity/sympathetic activity ratio. As indicated above, in many embodiments of this type of application, the subject methods are employed to treat a condition in the subject in order to achieve a desired therapeutic outcome. In certain embodiments, the condition being treated is a disease condition.

The subject methods find use in the treatment of a variety of different conditions in which an abnormality in a subject's autonomic nervous system exists. By "treatment" is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition.

A variety of subjects are treatable according to the subject methods. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. Human subject of both genders and at any stage of development (i.e., neonates, infant, juvenile, adolescent, adult) may be treated according to the present invention. While the present invention may be used for the treatment of a human subject, it is to be understood that the subject methods may also be carried-out on other animal subjects such as, but not limited to, mice, rats, dogs, cats, livestock and horses, e.g., for veterinary purposes, and for drug screening and drug development purposes. Accordingly, it is to be understood that any subject in need of being treated according to the subject invention is suitable.

Moreover, suitable subjects of this invention include those who have and those who have not previously been afflicted with a condition, those that have previously been determined to be at risk of suffering from a condition, and those who have been initially diagnosed or identified as being afflicted with or experiencing a condition.

As noted above, abnormalities in a subject's autonomic nervous system include, but are not limited to, those characterized by an abnormally high parasympathetic activity or abnormally low parasympathetic activity and/or an abnormally high sympathetic activity or abnormally low sympathetic activity, where in certain embodiments the parasympathetic activity and/or the sympathetic activity may be normal. For example, there are numerous conditions that the inventors of the subject invention have discovered are at least partially manifested by an abnormal sympathetic function, e.g., an abnormal balance of the sympathetic and parasympathetic functions of the autonomic nervous system, particularly those that manifest higher than normal (as defined by those seen in healthy individuals between the ages of about 20 to about 25 years old) sympathetic function or ratio of sympathetic function to parasympathetic function, which may be treated in accordance with the subject invention.

Examples of conditions that may be treated with the methods of the subject invention include, but are not limited to, neurodegenerative conditions including neurodegenerative diseases, e.g., Alzheimer's disease, Pick's disease, dementia, delirium, amyotrophic lateral sclerosis, and the like; neuroinflammatory conditions including neuroinflammatory diseases, e.g., viral meningitis, viral encephalitis, fungal meningitis, fungal encephalitis, multiple sclerosis, charcot joint; myasthenia gravis, and the like; orthopedic inflammatory conditions including orthopedic inflammatory diseases, e.g., osteoarthritis, inflammatory arthritis, regional idiopathic osteoporosis, reflex sympathetic dystrophy, Paget's disease, osteoporosis, and the like; lymphoproliferative conditions including lymphoproliferative diseases, e.g., lymphoma, lymphoproliferative disease, Hodgkin's disease, inflammatory pseudomotor of the liver, and the like; autoimmune conditions including autoimmmune diseases, e.g., Graves disease, raynaud's, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, Reiter's disease, lupus, and the like; inflammatory conditions, e.g., ARDS, multiple sclerosis, rheumatoid arthritis, juvenile rheumatoid arthritis, juvenile chronic arthritis, and the like; infectious diseases, e.g., sepsis, viral and fungal infections, diseases of wound healing, wound healing, tuberculosis, infection, AIDS, human immunodeficiency virus, and the like; pulmonary conditions including pulmonary diseases, e.g., tachypnea, fibrotic lung diseases such as cystic fibrosis and the like, interstitial lung disease, desquamative interstitial pneumonitis, non-specific interstitial pneumonitis, lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like; transplant-related conditions such as transplant related side effects such as transplant rejection, transplant-related tachycardia, transplant related renal failure, transplant related bowel dysmotility, transplant-related hyperreninemia, and the like; gastrointestinal conditions including gastrointestinal diseases, e.g., hepatitis, xerostomia, bowel mobility, peptic ulcer disease, constipation, ileus, irritable bowel syndrome, post-operative bowel dysmotility, inflammatory bowel disease, typhilitis, and the like; endocrine conditions including endocrine diseases, e.g., hypothyroidism, hyperglycemia, diabetes, obesity, syndrome X, insulin resistance, polycycstic ovarian syndrome ("PCOS"), and the like; genitourinary conditions including genitourinary diseases, e.g., renal failure, hyperreninemia, hepatorenal syndrome, renal tubular acidosis, pulmonary renal syndrome, and the like; skin conditions including skin diseases, e.g., wrinkles, cutaneous vasculitis, psoriasis, and the like; aging associated conditions including aging associated diseases, e.g., shy dragers, multi-system atrophy, age related inflammation conditions, cancer, and the like; neurologic conditions including neurologic diseases such as epilepsy, depression, schizophrenia, seizures, stroke, insomnia, cerebral vascular accident, transient ischemic attacks, stress, bipolar disorder, concussions, post-concussive syndrome, cerebral vascular vasospasm, central sleep apnea, obstructive sleep apnea, and the like; Th-2 dominant conditions including Th-2 dominant diseases, e.g., typhilitis, osteoporosis, lymphoma, myasthenia gravis, lupus, and the like; conditions, including diseases, that cause hypoxia, hypercarbia, hypercapnia, acidosis, acidemia, such as acute pulmonary embolism, sudden infant death syndrome ("SIDS"), sudden adult death syndrome ("SADS"), chronic pulmonary embolism, pleural effusion, cardiogenic pulmonary edema, non-cardiogenic pulmonary edema, acute respiratory distress syndrome (ARDS), neurogenic edema, hypercapnia, academia, renal tubular acidosis, lung diseases that causes acidosis, and the like; pediatric-related conditions including pediatric-related diseases, e.g., respiratory distress syndrome, sudden infant death syndrome, hirschsprung disease, bronchopulmonary dysplasia, congenital megacolon, aganglionosis, and the like; OB-GYN conditions including OB-GYN diseases, e.g., amniotic fluid embolism, menopausal mood disorders, premenstrual mood disorders, pregnancy-related arrhythmias, fetal stress syndrome, fetal hypoxia, amniotic fluid embolism, and the like; sudden death syndromes, e.g., sudden infant death syndrome, sudden adult death syndrome, and the like; fibrosis; post-operative recovery conditions such as post-operative pain, post operative ileus, post-operative fever, post-operative nausea, and the like; post-procedural recovery conditions such as post-procedural pain, post procedural ileus, post-procedural fever, post-procedural nausea, and the like; chronic pain; trauma; and the like; disorders of thermoregulation, and the like. Other conditions may also be treated in accordance with the subject invention, e.g., cyclic vomiting syndrome. Embodiments of the subject invention include treating one or more conditions, sequentially or at the same time, in accordance with the subject invention.

For example, conditions that promote maladaptive sympathetic bias may be treated with the subject invention. The inventors of the subject invention have realized that, unexpectedly, maladaptive sympathetic bias is a distinct syndrome that may be implicated in a number of fatal or potentially fatal conditions. Normally, the sympathetic drive is an adaptive response to dynamic physiological demands of the body. Under certain conditions, the response may become maladaptive. The inventors of the subject invention have realized that dramatic impacts on the health and well-being of an individual, in certain instances, may be related to acute sympathetic challenge in the context of background chronic sympathetic bias.

Chronic sympathetic bias may occur in various situations. For example, it may occur when the normal sympathetic bias fails to correct a precipitating respiratory or metabolic abnormality. The inventors of the subject invention have realized that conditions such as sudden infant death syndrome ("SIDS") and sudden adult death syndrome ("SADS") including sudden death among pregnant women, as well as others, may fall in this category and thus are conditions that may be treated, or rather prevented, by practicing the subject methods. Furthermore, sustained sympathetic bias is also noted during pregnancy, presumably as an adaptive response. Some diseases, such as pheochromocytoma, are intrinsically adrenergic. Sympathetic bias may also be a maladaptive component of the aging process attributable to an inexorable functional decline in autonomic regulatory systems. In the context of sympathetic bias, the inventors have realized that an acute sympathetic episode, as a centrally or peripherally mediated response to acute behavioral, metabolic, or physiologic stressors such as fear, injury, hypoxia, hypercarpnia, acidosis, sleep arousal, and physical activity, may increase the likelihood of certain conditions.

For example, conditions related to chronic or acute hypoxia, hypercarpnia and acidosis and other chronic conditions that disturb $pO_2$, $pCO_2$ and pH such as chronic obstructive pulmonary disease ("COPD"), primary pulmonary hypertension ("PPHTN"), secondary pulmonary hypertension ("SPHTN") and the like, may be treated in accordance with the subject invention. Specifically, the inventors of the subject invention have discovered that excess sympathetic activity relative to parasympathetic activity elicited through, or rather a centrally or peripherally mediated response to, various changes in $pO_2$, pH and $pCO_2$, accounts for many of the physiological consequences of chronic conditions that disturb $pO_2$, pCO2 and pH. chronic conditions that disturb $pO_2$, $pCO_2$ and pH levels such as COPD, PPHTN, SPHTN, and the like, e.g., by increasing the parasympathetic activity/sympathetic activity ratio.

As noted above, the subject methods may be employed to treat or rather prevent sudden infant death syndrome ("SIDS") and sudden adult death syndrome ("SADS"), including sudden death amongst pregnant women. In this regard, the inventors of the subject invention have discovered that in certain instances sympathetic bias may be implicated in SIDS and SADS.

More specifically, the inventors of the subject invention have realized that a maladaptive shift to sympathetic bias may be a key determinant of SIDS. Heart rate variability (HRV) is often used as a measure of autonomic balance. Decreased HRV, indicating sympathetic bias, has been observed in patients with central hypoventilation and in infants who have later succumbed to SIDS (see for example Edner A, Katz-Salamon M, Lagercrantz H, Ericson M, Milerad J. Heart rate variability in infants with apparent life-threatening events. Acta Paediatr. 2000 November; 89 (11):1326-9). This finding is consistent with other conditions of hypoxia such as respiratory distress syndrome and prenatal hypoxia which decrease HRV and induce tachycardia (see for example Aarimaa T, Oja R. Transcutaneous PO2, $PCO_2$ and heart rate patterns during normal postnatal adaptation and respiratory distress. Early Hum Dev. 1988 January; 16 (1):3-11), both indicators of sympathetic bias. Infants who experience near-miss SIDS demonstrate tachycardia and decreased HRV (see for example Reid G M. Sudden infant death syndrome: neonatal hypodynamia (reduced exercise level). Med Hypotheses. 2001 March; 56 (3):280-5). Food regurgitation and diaphoresis associated with SIDS may reflect excess sympathetic activity (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; Guntheroth W G, Spiers P S. Thermal stress in sudden infant death: Is there an ambiguity with the rebreathing hypothesis? Pediatrics. 2001 April; 107 (4):693-8; Uchino M, Ishii K, Kuwahara M, Ebukuro S, Tsubone H. Role of the autonomic nervous system in emetic and cardiovascular responses in Suncus murinus. Auton Neurosci. 2002 Sep. 30; 100 (1-2):32-40).

Inciting causes of sympathetic bias may be manifold. Hyperthermia and fever, both of which have known associations with SIDS (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; Guntheroth W G, Spiers P S. Thermal stress in sudden infant death: Is there an ambiguity with the rebreathing hypothesis? Pediatrics. 2001 April; 107 (4):693-8) are hyperadregnergic states (see for example Rowell L B. Hyperthermia: a hyperadrenergic state. Hypertension. 1990 May; 15 (5):505-7). Infection and inflammation, which are associated with SIDS (see for example Krous H F, Nadeau J M, Silva P D, Blackbourne B D. A comparison of respiratory symptoms and inflammation in sudden infant death syndrome and in accidental or inflicted infant death. Am J Forensic Med Pathol. 2003 March; 24 (1):1-8.), are also potential causes of sympathetic bias. In certain situations, the adaptive chemoreceptor-mediated sympathetic response of arousal and increased respiration may fail to correct the underlying hypoxia, hypercapnia, and acidosis, leading to a maladaptive sympathetic bias. The association of prone sleeping position, obstructive sleep apnea, and other respiratory conditions with SIDS (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; American Academy of Pediatrics, Task Force on Infant Sleep Position and Sudden Infant Death Syndrome. Changing concepts of sudden infant death syndrome: implications for infant sleeping environment and sleep position. Pediatrics. 2000; 105:650-656; Hoffman H J, Damus K, Hillman L, Krongrad E. Risk factors for SIDS: results of the National Institute of Child Health and Human Development SIDS Cooperative Epidemiological Study. Ann N Y Acad Sci 1988; 533: 13-30) may exemplify this phenomenon. In infants with OSA, as with their adult counterparts, the sympathetic bias can exacerbate sleep disturbance and can trigger insomnia (see for example Harrison G A. Stress, catecholamines, and sleep. Aviat Space Environ Med 1985; 56:651-653; Montagna P, Gambetti P, Cortelli P, Lugaresi E. Familial and sporadic fatal insomnia. Lancet Neuro 2003 March; 2 (3):167-176.), leading to a pernicious cycle.

Sympathetic bias has an association with QT interval prolongation, a risk factor for sudden cardiac death in adults (see for example Esposito K, Marfella R, Gualdiero P, Carusone C, Pontillo A, Giugliano G, Nicoletti G, Giugliano D. Sympathovagal Balance, Nighttime Blood Pressure, and QT Intervals in Normotensive Obese Women. Obes Res. 2003 May; 11 (5):653-9). Sympathetic bias may predispose infants to similar risks. A significant association between prolonged QT interval and SIDS victims or those who experienced apparent life-threatening event (ALTE) has been noted (see for example Goldhammer E I, Zaid G, Tal V, Jaffe M, Abinader E G. QT dispersion in infants with apparent life-threatening events syndrome. Pediatr Cardiol. 2002 November-December; 23 (6):605-7; Schwartz P J, Stramba-Badiale M, Segantini A, et al. Prolongation of the QT interval and the sudden infant death syndrome. N Engl J Med. 1998; 338:1709-1714). Various theories for this association have been proposed, including development-related abnormalities in cardiac sympathetic innervation and genetic predisposition (see for example Stramba-Badiale M, Lazzarotti M, Schwartz P J. Development of cardiac innervation, ventricular fibrillation, and sudden infant death syndrome. Am J Physiol 1992; 263:H1514-H1522; Ackerman, M. J., Siu, B. L., Sturner, W. Q., Tester, D. J., Valdivia, C. R., Makielski, J. C., Towbin, J. A. (2001). Postmortem Molecular Analysis of SCNSA Defects in Sudden Infant Death Syndrome. JAMA 286: 2264-2269; Schwartz P J. Cardiac sympathetic innervation and the sudden infant death syndrome: a possible pathogenetic link. Am J Med 1976; 60:167-172). The inventors of the subject methods have realized that maladaptive sympathetic response is the key determinant of SUDS, a broader view than that which had been held prior to the inventor's view.

The inventors of the subject invention have also realized that sudden death precipitated by maladaptive sympathetic bias, similar to those seen in infants, may account for a proportion of SADS cases.

For example, while obviously multifactorial in mechanism, conditions such as constipation, insomnia, hypertension are endemic among the aged and are consistent with a broad physiologic bias towards sympathetic function. HRV and baroreflex sensitivity decreases with aging (see for example Stratton J R, Levy W C, Caldwell J H, Jacobson A, May J, Matsuoka D, Madden K. Effects of aging on cardiovascular responses to parasympathetic withdrawal. J Am Coll Cardiol. 2003 Jun. 4; 41 (11):2077-83), consistent with a shift to sympathetic bias. The inventors have realized that, as in SIDS, some cases of SADS may reflect maladaptive chemoreceptor response to hypoxia, hypercapnia, and acidosis, all of which are common conditions seen in the elderly due to myriad of diseases. Examples of chronic diseases that exemplify this phenomenon include, but are not limited to, renal failure, congestive heart failure, chronic obstructive lung disease ("COPD") and chronic pain (see for example Wiggers H, Botker H E, Egeblad H, Christiansen E H, Nielsen T T, Molgaard H. Coronary artery bypass surgery in heart failure patients with chronic reversible and irreversible myocardial dysfunction: effect on heart rate variability. Cardiology. 2002; 98 (4):181-5). Heightened sympathetic function is seen in many other conditions including pheochromocytoma, autoimmune conditions, and collagen vascular diseases (see for example Lagana B, Gentile R, Vella C, Giovani A, Tubani L, Mastrocola C, Baratta L, Bonomo L. Heart and autonomic nervous system in connective tissue disorders. Recenti Prog Med. 1997 December; 88 (12)579-84; P. K. Stein, P. Nelson, J. N. Rottman et al., Heart rate variability reflects severity of COPD in PiZ alpha-1-antitrypsin deficiency. Chest 113 (1998), pp. 327-333). More broadly, the inventors have realized that attrition of parasympathetic function with aging may be an important but until now, unrecognized, culprit in generalized sympathetic bias of aging. For example, it has been observed that QT interval lengthens with aging and other chronic conditions that promote sympathetic bias such as COPD (see for example Wei, J. Y., Spurgeon, H. A. and Lakatta, E. G. (1984) Excitation-contraction in rat myocardium: alteration with adult aging. Am. J. Physiol. 246, H784-H791; Tukek T, Yildiz P, Atilgan D, Tuzcu V, Eren M, Erk O, Demirel S, Akkaya V, Dilmener M, Korkut F. Effect of diurnal variability of heart rate on development of arrhythmia in patients with chronic obstructive pulmonary disease. Int J Cardiol. 2003 April; 88 (2-3):199-206), putting the patient at increased risk of fatal arrhythmias.

Still further, pregnant women may exhibit various signs of sympathetic bias such as hyperemesis, hypertension, and increased cardiac output, and as such may be treated in accordance with the subject invention. More specifically, the inventors of the subject invention have realized that sympathetic bias in pregnant women may be responsible for sudden death in pregnant women. The shift to sympathetic bias may represent adaptations to the physiologic and immunologic demands of gestation (see for example Minagawa M, Narita J, Tada T, Maruyama S, Shimizu T, Bannai M, Oya H, Hatakeyama K, Abo T. Mechanisms underlying immunologic states during pregnancy: possible association of the sympathetic nervous system. Cell Immunol. 1999 Aug. 25; 196 (1):1-13). Pregnancy is associated with QT prolongation, increased plasma catecholamine levels, and decreased HRV, similar to the other augmented sympathetic states that increase risk for sudden death (see for example Gowda R M, Khan I A, Mehta N J, Vasavada B C, Sacchi T J. Cardiac arrhythmias in pregnancy: clinical and therapeutic considerations. Int J Cardiol. 2003 April; 88 (2-3): 129-33; N. D. Averyl, L. A. Wolfe, C. E. Amara, G. A. L. Davies, and M. J. McGrath. Effects of human pregnancy on cardiac autonomic function above and below the ventilatory threshold J Appl Physiol 90: 321-328, 2001; Vol. 90, Issue 1, 321-328, January 2001). While an increase rate of sudden deaths from arrhythmias has been noted in pregnant women and has been attributed to hormonal influences (see for example Wolbrette D. Treatment of arrhythmias during pregnancy. Curr Womens Health Rep. 2003 April; 3 (2): 135-9; Wolbrette D, Naccarelli G, Curtis A, Lehmann M, Kadish A. Gender differences in arrhythmias. Clin Cardiol. 2002 February; 25 (2):49-56), the subject inventors have realized that sympathetic excess of pregnancy may be a potential cause. The most common manifestation of exaggeration of the normal sympathetic shift in pregnant women may be pre-eclampsia, which accounts for 80% of maternal mortality in developing countries (see for example Conz P A, Catalano C. Pathogenesis of pre-eclampsia. G Ital Nefrol. 2003 January-February; 20 (1):15-22). Measurement of post-ganglionic action potentials reveal mean sympathetic activity to be three times higher in pre-eclamptic women compared with healthy pregnant women, and two times higher compared with the hypertensive non-pregnant women (see for example Schobel H P, Fischer T, Heuszer K, Geiger H, Schmieder R E. Preeclampsia—a state of sympathetic overactivity. N Engl J Med 1996; 335:1480-1485). HRV is reduced in pre-eclamptic women (see for example Yang C C, Chao T C, Kuo T B, Yin C S, Chen H I. Preeclamptic pregnancy is associated with increased sympathetic and decreased parasympathetic control of HR. Am J Physiol Heart Circ Physiol. 2000 April; 278 (4):H1269-73). Autonomic imbalance appears to particularly affect the central nervous system. Seizures, a common morbidity of pre-eclampsia, and acute cerebral vasoconstriction, the most common cause of mortality, may both be viewed as acute adrenergic phenomenon (see for example Novak V V, Reeves L A, Novak P, Low A P, Sharbrough W F. Time-frequency mapping of R-R interval during complex partial seizures of temporal lobe origin. J Auton Nery Syst. 1999 Sep. 24; 77 (2-3):195-202). Seizure is also a common presentation among the aged, with 25% of new cases of epilepsy diagnosed in the elderly (see for example Stephen L J, Brodie M J. Epilepsy in elderly people. Lancet. 2000 Apr. 22; 355 (9213):1441-6).

The inventors of the subject invention have also discovered that many conditions of aging are manifestations of sympathetic bias that is unmasked by withdrawal of autonomic function, particularly the parasympathetic system. For example, in regards to employing the subject methods in the treatment of aging associated conditions, the inventors of the subject invention have realized that many clinical consequences of aging are pleiotropic manifestations of the loss of parasympathetic function that occurs during post-reproductive senescence. The inventors realized that the loss of parasympathetic function unmasks the baseline sympathetic bias inherent in the end-organs, resulting in the familiar signs of aging including tachycardia, constipation, insomnia, erectile dysfunction, fluid retention, and systemic inflammation. These consequences in turn may contribute to many of the common diseases associated with aging including type-2 diabetes, Alzheimer's, cancer, and the like. Maintenance and restoration of parasympathetic function may enable upstream control over the deleterious aspects of inherent end-organ adrenergic bias.

More specifically, aging is marked by a compendium of physiologic and biologic dysfunctions. The inventors of the subject invention have realized that many seemingly unrelated consequences of aging are, at least in part, manifestations of a single upstream phenomenon: an emergent sympathetic bias that is unmasked by loss of parasympathetic function during post-reproductive senescence and may be treated using the subject methods. Common symptomatic presentations among the elderly include dysphagia, constipation, insomnia, anorexia, and the like. These symptoms are the final common pathways of many different complex physiologic disturbances and iatrogenic circumstances. These symptoms also represent the classic organ-specific manifestations of excess adrenergic tone.

The inventors of the subject invention realized that if sympathetic excess is the dominant biologic theme during senescence, the mechanisms may be a loss of parasympathetic function. It is known that the vagus nerve shows decreased activity with age (see for example Tulppo M. P., Makikallio T. H., Seppanen T., et al. Vagal modulation of heart rate during exercise: effects of age and physical fitness. Am J Physiol 1998 February; 274 (2 Pt 2): H424-9). In the gastrointestinal system, the attrition of vagal and myenteric innervation has been noted with advancing age (see for example Phillips R. J., Powley T. L. As the gut ages: timetables for aging of innervation vary by organ in the Fischer 344 rat. J Comp Neurol 2001 Jun. 4; 434 (3):358-77). In the bladder, waning parasympathetic function has been noted and is one of the targets for treating dysfunctional bladder (see for example Anderson K. E., Hedlund P. Pharmacologic perspective on the physiology of the lower urinary tract. Urology 2002 November; 60(5 Suppl 1):13-20). Accordingly, the subject methods may be employed to decrease or inhibit sympathetic activity at least by administration of at least one beta-blocker and increase or stimulate parasympathetic function.

Accordingly, the inventors of the subject invention realized that the end-organs of autonomic innervation are intrinsically sympathetic, thus resulting in the failure of the autonomic system to rebalance through the reduction of sympathetic tone-thereby offsetting the lost parasympathetic function-as vagal innervation generally wanes with aging. Accordingly, the inventors of the subject invention have realized that the end-organs of autonomic innervation are instrinsically sympathetic, and in the absence of regulation, they exhibit tonically adrenergic activity that cannot be mitigated by a decrease in extrinsic sympathetic signal. As such, the inventors of the subject invention realized that the excess sympathetic tone is not likely to be attributable to generalized elevation in circulating catecholamines. Thus, the loss of parasympathetic function with aging may be viewed as the unmasking the intrinsic sympathetic activity of end-organs, yielding clinical consequences similar to those associated with aging. Accordingly, the inventors of the subject invention have realized that such conditions may be treated with the subject invention, e.g., by decreasing or inhibiting sympathetic activity at least by administration of at least one beta-blocker and increasing or stimulating parasympathetic function.

One of the most profound iterations of this theme may be the link between the autonomic and immune systems, in particularly the link between autonomic balance and Th-1/Th-2 balance. The superimposition of lifespan data on autonomic balance and Th-1/Th-2 balance (graph 1) demonstrates simultaneous peaking of relative parasympathetic and Th-1 functions during reproductive adulthood, followed by a gradual loss of these functions during the ensuing senescence. Co-migration of these functions over the lifespan suggests some link between the two functions and the autonomic system may in part be responsible for governing Th-1/Th-2 balance both regionally and systemically through innervations of various targets including the adrenal glands and lymphoid tissues.

The inventors of the subject invention have realized the dysregulation of inflammation resulting from the waning parasympathetic tone may be implicated in the susceptibility of the elderly to many other conditions such as atherosclerotic disease, cancer, osteoporosis, viral infections, allergic conditions, and sepsis. As such, the subject methods may be employed to modulating a subject's autonomic nervous to treat aging-related conditions, including age-related disease conditions, e.g., by decreasing or inhibiting sympathetic activity at least by administration of at least one beta-blocker and increasing or stimulating parasympathetic function.

Accordingly, as described above, the subject methods may be employed in the treatment of a wide variety of conditions. For example, as described above, the subject methods may also be employed to treat neurodegenerative conditions including diseases. Branches of the autonomic nervous system that may be modulated in accordance with the subject invention to treat neurodegenerative diseases include parasympathetic nerve and ganglia such as, but not limited to one or more of the vagus nerve, cranial nerve III, cranial nerve VII, cranial nerve IX, sphenopalatine ganglion, ciliary ganglion, submandibular ganglion, otic ganglion and/or sympathetic nerve and ganglia such as, but not limited to one or more of cervical sympathetic ganglia.

Branches of the autonomic nervous system that may be modulated in accordance with the subject invention to treat orthopedic inflammatory diseases including diseases include parasympathetic nerve and ganglia such as, but not limited to one or more of the vagus nerve and/or sympathetic nerve and ganglia such, but not limited to one or more of the spinal nerves (dorsal and ventral rami), postganglionic fibers to spinal nerves (innervating skin, blood vessels, muscle, adipose tissue) and sympathetic chain ganglia.

Branches of the autonomic nervous system that may be modulated in accordance with the subject invention to treat inflammatory conditions including diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus and pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat lymphoproliferative conditions including diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus and pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat inflammatory conditions including diseases and infectious diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat pulmonary conditions including diseases include parasympathetic nerve and ganglia such as, but not limited to one or more of the vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat gastrointestinal conditions including diseases include parasympathetic nerve and ganglia such as, but not limited to one or more of the vagus nerve, celiac plexus, hypogastric plexus, pelvic nerves and/or sympathetic nerve and ganglia such as, but not limited to one or more of the sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat endocrine conditions including diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat genitourinary conditions including diseases include parasympathetic nerve and ganglia such as, but not limited to one or more of the vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat skin conditions including diseases include parasympathetic nerve and ganglia such as, but not limited to one or more of the vagus nerve and/or sympathetic nerve and ganglia such as, but not limited to one or more of the cervical sympathetic ganglia such as, but not limited to one or more of the spinal nerves (dorsal and ventral rami), postganglionic fibers to spinal nerves (innervating skin, blood vessels, sweat glands, erector pili muscle, adipose tissue), sympathetic chain ganglia and coccygeal ganglia.

Branches of the autonomic nervous system that may be modulated in accordance with the subject invention to treat aging associated conditions including diseases, including diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat Th-2 dominant conditions including diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat neurologic conditions including diseases include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat conditions, including diseases, that cause hypoxia, hypercarbia, acidosis, acidemia, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Devices and Systems

The subject invention also includes devices and systems that may be employed in the practice of the subject methods. The subject systems at least include an effective amount of at least one beta-blocker. The beta-blocker may be in any suitable formulation or form. For example, a system may include a beta-blocker composition for transdermal administration, e.g., present as an active agent of a transdermal patch, film or the like, an oral dosage form, injection dosage form, etc. Additional pharmacological agents may also be included in systems of the subject invention.

In certain embodiments, the subject systems may also include suitable delivery means, dictated by the particular beta-blocker and/or pharmacological agent as describe above, e.g., the particular form of the agent such as whether the beta-blocker and/or other pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, intravaginal, endocervical, intrathecal, intranasal, intravesicular, on the eye, in the ear canal, etc. Accordingly, certain systems may include a suitable drug delivery device, e.g., a suppository applicator, syringe, I.V. bag and tubing, electrode, an implantable drug delivery device, an electric energy applying device, and the like.

Systems may also include one or more devices for delivering, e.g., implanting, a component such as a drug delivery device, an electrosurgical device, and the like, to a target site of a subject such as into the body cavity of a subject. For example, an endoscope, introducer needle, and the like, may be provided. Systems may also include one or more imaging or scanning apparatuses such as a fluoroscope, CT scan, and the like.

The subject systems may also include an electric energy applying device such that a system according to the present invention may include at least one electrode for electrically modifying at least a portion of a subject's autonomic nervous system. In certain embodiments the electric energy applying device is an implantable device, or at least certain components such as one or more electrodes, may be implantable. Certain embodiments may include a plurality of electrodes, where some or all may be the same or some or all may be different. For example, at least a first electrode may be provide for electrically stimulating at least a portion of the parasympathetic system and at least a second electrode may be provided for inhibiting activity in at least a portion of the sympathetic system. In certain embodiments, a "test" electrode, as described above, may be included in a system. As noted above, such "test" electrodes may be a radiofrequency stimulating electrode. Still further, one or more electrodes may be included in a system which, instead of or in addition to delivering electric impulses to at least a portion of the autonomic nervous system, delivers an autonomic nervous system pharmacological agent to at least a portion of the autonomic nervous system, e.g., may be used to deliver at least one beta-blocker. Included may be an energy source such as a battery or generator, where in certain embodiments the energy source may be implantable, and may also include one or more leads or wires for coupling the one or more electrodes to an energy source.

A system for use in practicing the subject methods may also include a suitable detector for detecting one or more physical and/or chemical aspects related to the autonomic nervous system. The detector at least includes data gathering means. Also provided may be data analysis means where such may be a separate component from or integral with data gathering means, but in many embodiments is operatively coupled to data gathering means, e.g., integral with. In use, data related to one or more aspects of the autonomic nervous system may be collected by data gathering means and forwarded to data analysis means which executes steps necessary to process and evaluate the collected data and determine whether the autonomic nervous system is in need of electrical modulation. Such evaluation may include comparing data to reference values, etc. When present, a detector (or data evaluation means if separate) may be operatively coupled to one or more other elements of a given drug delivery means and/or electric energy applying device such that results of the determinations of autonomic modulation may automatically trigger (or cease) activation of drug delivery and/or electrical energy to the autonomic nervous system. Suitable detectors include any detector capable of gathering information about the autonomic nervous system and includes both invasive, minimally invasive and non-invasive detectors where in certain embodiments a detector may be an implantable detector. Suitable detectors include, but are not limited to, those capable of collecting data regarding nerve conduction, circulating catecholamine levels, heart rate variability ("HRV"), post-ganglionic action potentials, QT interval, and the like and include, but are not limited to, MRI apparatuses, CT apparatus, neurography apparatuses, cardiovascular monitors, sensors including electrodes, etc.

Computer Readable Mediums and Programming Stored Thereon

Any part of the subject methods, e.g., detection, analysis and activation/termination of drug delivery and/or electrical energy including selecting suitable drug delivery parameters and/or electrical parameters, may be performed manually or automatically. For example, the subject invention may include suitable computing means such as suitable hardware/software for performing one or more aspects of the subject methods. For example, one or more aspects of the subject invention may be in the form of computer readable media having programming stored thereon for implementing the subject methods. Accordingly, programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out some or all of the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means (i.e., information collected by data gathering means about the autonomic nervous system) and process that information to determine the state of the autonomic nervous system, e.g., the activity level of the parasympathetic system and/or the sympathetic system and even whether the autonomic nervous system requires modulation, e.g., if the parasympathetic activity is normal or abnormal and/or if sympathetic activity is normal or abnormal, and, if so, the specifics of the modulation that may be required, e.g., to treat a condition. The result of that processing may be communicated to a user, e.g., via audio and/or visual means, e.g., the algorithm may also include steps or functions for generating a variety of autonomic nervous system profile graphs, plots, etc.

The algorithm may be configured to, or otherwise be capable of, directing a microprocessor to activate, i.e., turn "on" and "off" a drug delivery device, e.g., an implantable or external drug delivery device and/or an electric energy applying device for applying energy to at least a part of the autonomic nervous system, e.g., in response to the above-described determination of the state of the autonomic nervous system. For example, if it is determined that sympathetic activity needs to be decreased, the processor may direct a drug delivery device to provide the appropriate amount of drug or otherwise execute a suitable drug treatment regime to result in the desired action.

The subject invention may also include a data set of known or reference information stored on a computer readable medium to which autonomic nervous system data collected may be compared for use in determining the state of the autonomic nervous system. The data may be stored or configured in a variety of arrangements known to those of skill in the art.

Kits

Also provided are kits for practicing the subject methods. While the subject kits may vary greatly in regards to the components included, typically, the kits at least include at least one beta-blocker in a suitable form. The subject kits may also include one or more other pharmacological agents. The dosage amount of the one or more beta-blockers and/or other pharmacological agents provided in a kit may be sufficient for a single application or for multiple applications. Accordingly, in certain embodiments of the subject kits a single dosage amount of a beta-blocker and/or a single dosage of at least one another, different pharmacological agent is present.

In certain other embodiments, multiple dosage amounts of a beta-blocker and/or one other pharmacological agent may be present in a kit. In those embodiments having multiple dosage amounts of, e.g., at least one beta-blocker, such may be packaged in a single container, e.g., a single tube, bottle, vial, and the like, or one or more dosage amounts may be individually packaged such that certain kits may have more than one container of a beta-blocker.

Suitable means for delivering one or more beta-blockers and/or other pharmacological agents to a subject may also be provided in a subject kit. The particular delivery means provided in a kit is dictated by the particular beta-blocker and/or pharmacological agent employed, as describe above, e.g., the particular form of the beta-blocker and/or other agent such as whether the beta-blocker and/or other pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intravaginal, endocervical, intrathecal, intranasal, intravesicular, on the eye, in the ear canal, intraperiactivityal, intradermal, transdermal, intracheal, etc. Accordingly, certain systems may include a suppository applicator, syringe, I.V. bag and tubing, electrode, transdermal patch or film, etc.

The subject kits also include instructions for how to practice the subject methods and in particular how to administer the at least one beta-blocker provided in the kit to treat a subject for a condition caused by an abnormality in the subject's autonomic nervous system by pharmacologically modulating at least a portion of the subject's autonomic nervous system to decrease sympathetic activity to treat a condition. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the interne, are provided. An example of this embodiment is a kit that includes a web address where the instructions can be viewed and/or from which the instructions can be downloaded. As with the instructions, this means for obtaining the instructions is recorded on a suitable substrate.

Kits may also include an electric energy applying device, as described above. Accordingly, subject kits may include an electric energy applying device such that they may include at least one electrode for electrically modifying at least a portion of a subject's autonomic nervous system in accordance with the subject invention, as described above. In many embodiments, the electric energy applying device provided in a kit is an implantable device, or at least certain components such as one or more electrodes, are implantable. Certain kits may include a plurality of electrodes, where some or all may be the same or some or all may be different. For example, certain kits may include at least a first electrode for electrically stimulating at least apportion of the parasympathetic system and at least a second electrode for inhibiting activity in at least a portion of the sympathetic system. In certain embodiments, a subject kit may include a "test" electrode, as described above such as a radiofrequency stimulating electrode. Still further, one or more electrodes may be included in a kit which, instead of or in addition to delivering electric impulses to at least a portion of the autonomic nervous system, delivers an autonomic nervous system pharmacological agent to at least a portion of the autonomic nervous system. Kits according to the subject invention typically also include an energy source such as a battery or generator, where in certain embodiments the energy source may be implantable, and may also include one or more leads or wires for coupling the one or more electrodes to an energy source.

Devices for delivering, e.g., implanting, an electrosurgical device and/or a drug delivery device to a target site of a subject such as into the body cavity of a subject may also be included in the subject kits. For example, an endoscope, introducer needle, and the like may be provided.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is evident from the above discussion that the above described invention provides methods, system and kits for treating a subject for a condition caused by an autonomic nervous system abnormality in a subject which are easy to use, effective, and which may be used to treat variety of different conditions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for an inflammatory respiratory condition caused by an autonomic nervous system abnormality characterized by a sympathetic bias, the method comprising:
    modulating at least a portion of said subject's autonomic nervous system by administering an effective amount of a beta-blocker to said subject to treat said subject for an inflammatory respiratory condition wherein the inflammatory respiratory condition is acute respiratory distress syndrome and wherein said beta-blocker is chosen from atenolol, betaxolol, bisoprolol, carvedilol, esmolol, labetalol, metoprolol, nadolol, pindolol, propranolol, sotalol, timolol, acebutalol, oxprenolol, carvedilol, and entbutolol.

2. The method according to claim 1, wherein said modulation results in a parasympathetic bias in at least a portion of said autonomic nervous system.

3. The method according to claim 1, wherein said modulating results in a substantially equal parasympathetic and sympathetic functions in at least a portion of said autonomic nervous system.

4. The method of claim 1, wherein said abnormality comprises an abnormally low parasympathetic activity.

5. The method of claim 4, wherein said abnormality comprises normal sympathetic activity.

6. The method of claim 4, wherein said abnormality comprises an abnormally high sympathetic activity.

7. The method of claim 4, further comprising increasing said abnormally low parasympathetic activity.

8. The method of claim 1, wherein said method comprises increasing the parasympathetic activity/sympathetic activity ratio in at least a portion of said subject's autonomic nervous system.

9. The method of claim 1, wherein said beta-blocker is administered orally at least once a day to said subject.

10. The method of claim 1, wherein the method further comprises determining the state of the subject's autonomic nervous system by measuring a parasympathetic activity/sympathetic activity ratio in at least a portion of the subject's autonomic nervous system.

11. The method of claim 1, wherein the modulating comprises administering at least two different beta-blocker protocols.

12. The method of claim 1, wherein the subject is an adult.

* * * * *